(12) United States Patent
Fraser

(10) Patent No.: US 12,157,910 B2
(45) Date of Patent: Dec. 3, 2024

(54) SAMPLE PREPARATION FOR NUCLEIC ACID AMPLIFICATION

(71) Applicant: ILLUMINA CAMBRIDGE LIMITED, Nr Saffron Walden (GB)

(72) Inventor: Louise Fraser, Nr Saffron Walden (GB)

(73) Assignee: ILLUMINA CAMBRIDGE LIMITED, Nr Saffron Walden (GB)

( * ) Notice: Subject to any disclaimer, the term of this patent is extended or adjusted under 35 U.S.C. 154(b) by 122 days.

(21) Appl. No.: 15/741,983

(22) PCT Filed: Jul. 5, 2016

(86) PCT No.: PCT/GB2016/052026
§ 371 (c)(1),
(2) Date: Jan. 4, 2018

(87) PCT Pub. No.: WO2017/006108
PCT Pub. Date: Jan. 12, 2017

(65) Prior Publication Data
US 2018/0201974 A1    Jul. 19, 2018

Related U.S. Application Data

(60) Provisional application No. 62/189,063, filed on Jul. 6, 2015.

(51) Int. Cl.
C12Q 1/68 (2018.01)
C12Q 1/6806 (2018.01)
C12Q 1/6844 (2018.01)

(52) U.S. Cl.
CPC ......... *C12Q 1/6806* (2013.01); *C12Q 1/6846* (2013.01)

(58) Field of Classification Search
CPC .. C12Q 1/6806; C12Q 1/6846; C12Q 1/6886; C12Q 1/6869; C12Q 2600/156
See application file for complete search history.

(56) References Cited

U.S. PATENT DOCUMENTS

| | | |
|---|---|---|
| 5,043,272 A | 8/1991 | Hartley |
| 5,130,238 A | 7/1992 | Malek |
| 5,185,243 A | 2/1993 | Ullman |
| 5,455,166 A | 10/1995 | Walker |
| 5,573,907 A | 11/1996 | Carrino |
| 5,679,524 A | 10/1997 | Nikiforov |
| 6,172,218 B1 | 1/2001 | Brenner |
| 6,210,891 B1 | 4/2001 | Nyren |
| 6,214,587 B1 | 4/2001 | Dattagupta |
| 6,258,568 B1 | 7/2001 | Nyren |
| 6,274,320 B1 | 8/2001 | Rothberg |
| 6,306,597 B1 | 10/2001 | Macevicz |
| 6,969,488 B2 | 11/2005 | Bridgham |
| 7,001,792 B2 | 2/2006 | Sauer |
| 7,057,026 B2 | 6/2006 | Barnes |
| 7,211,414 B2 | 5/2007 | Hardin |
| 7,315,019 B2 | 1/2008 | Turner |
| 7,329,492 B2 | 2/2008 | Hardin |
| 7,405,281 B2 | 7/2008 | Xu |
| 7,427,673 B2 | 9/2008 | Balasubramanian |
| 7,582,420 B2 | 9/2009 | Oliphant |
| 7,670,810 B2 | 3/2010 | Gunderson |
| 8,728,764 B2 | 5/2014 | Boutell |
| 8,771,951 B2* | 7/2014 | Hogan ............... C12Q 1/689 435/6.12 |
| 8,951,781 B2 | 2/2015 | Reed |
| 9,017,942 B2* | 4/2015 | Shoemaker ......... C12Q 1/6881 435/6.1 |
| 9,938,575 B2* | 4/2018 | Tischfield ............ C12Q 1/6876 |
| 2005/0100900 A1 | 5/2005 | Kawashima |
| 2006/0099627 A1 | 5/2006 | Kara et al. |
| 2006/0188901 A1 | 8/2006 | Barnes |
| 2006/0240439 A1 | 10/2006 | Smith |
| 2006/0281109 A1 | 12/2006 | Ost |
| 2007/0166705 A1 | 7/2007 | Milton |
| 2008/0108082 A1 | 5/2008 | Rank |
| 2008/0108515 A1 | 5/2008 | Gormley et al. |
| 2008/0242555 A1 | 10/2008 | Shen et al. |
| 2009/0026082 A1 | 1/2009 | Rothberg |
| 2009/0042290 A1 | 2/2009 | Steele et al. |
| 2009/0127589 A1 | 5/2009 | Rothberg |
| 2010/0111768 A1 | 5/2010 | Banerjee |
| 2010/0137143 A1 | 6/2010 | Rothberg |
| 2010/0282617 A1 | 11/2010 | Rothberg |
| 2011/0236891 A1 | 9/2011 | Li et al. |

(Continued)

FOREIGN PATENT DOCUMENTS

| | | |
|---|---|---|
| CN | 102242189 | 11/2011 |
| CN | 102344919 | 2/2012 |

(Continued)

OTHER PUBLICATIONS

Walsh et al. (PNAS, 2010, 107(28):12629-12633) (Year: 2010).*
Laberge et al, (Appl Environ Microbiol, 1996, 62(9):3259-3264) (Year: 1996).*
Hsieh et al. (Acc Chem Res, 2015, 48:911-920) (Year: 2015).*
Ahmed et al. (Food Control 2010, vol. 21, p. 599-605) (Year: 2010).*
Leese et al. (Linnol Oceanogr.: Methods, 2008, 6:412-416) (Year: 2008).*
Rautio et al. (J of Microbiol Methods, 2006, vol. 65:404-416) (Year: 2006).*

(Continued)

*Primary Examiner* — Stephanie K Mummert
(74) *Attorney, Agent, or Firm* — STERNE, KESSLER, GOLDSTEIN & FOX P.L.L.C.

(57) ABSTRACT

Presented herein are methods and compositions for targeted amplification of DNA and sample identification. The methods are particularly useful in validation and quality control of samples and to confirm that WGS sequence data is properly paired with a patient sample prior to delivering sequence data to a physician or to a patient.

20 Claims, 16 Drawing Sheets

(56) References Cited

U.S. PATENT DOCUMENTS

| | | |
|---|---|---|
| 2012/0270305 A1 | 10/2012 | Reed |
| 2013/0065223 A1 | 3/2013 | Klein et al. |
| 2013/0079232 A1 | 3/2013 | Kain |
| 2013/0260372 A1 | 10/2013 | Buermann |

FOREIGN PATENT DOCUMENTS

| | | | |
|---|---|---|---|
| CN | 103710323 | 4/2014 | |
| EP | 0320308 | 6/1989 | |
| EP | 0336731 | 10/1989 | |
| EP | 0439182 | 7/1991 | |
| EP | 2159285 A2 * | 3/2010 | ........ B01L 3/502707 |
| EP | 2388312 | 11/2011 | |
| WO | WO 1989/09835 | 10/1989 | |
| WO | WO 1989/12696 | 12/1989 | |
| WO | WO 1990/01069 | 2/1990 | |
| WO | WO 1991/06678 | 5/1991 | |
| WO | WO 2004/018497 | 6/2004 | |
| WO | WO-2005021804 A1 * | 3/2005 | ........... C12Q 1/6827 |
| WO | WO-2005024021 A1 * | 3/2005 | ........... C12Q 1/6816 |
| WO | WO 2005/065814 | 7/2005 | |
| WO | WO 2006/064199 | 6/2006 | |
| WO | WO 2007/010251 | 1/2007 | |
| WO | WO 2007/123744 | 11/2007 | |
| WO | WO2009/016652 | 2/2009 | |
| WO | WO2010/038042 | 4/2010 | |
| WO | WO2011/025477 | 3/2011 | |
| WO | WO 11/104027 | 9/2011 | |
| WO | WO2012/034030 | 3/2012 | |
| WO | WO2013/131962 | 9/2013 | |
| WO | WO 2015/057985 | 4/2015 | |
| WO | WO 2015/106941 | 7/2015 | |
| WO | WO 2015/108663 | 7/2015 | |
| WO | WO 2015/189588 | 12/2015 | |
| WO | WO2017/006108 | 1/2017 | |

OTHER PUBLICATIONS

Hamaguchi et al. (Clin Chem, 1998, 44:11, p. 2256-2263) (Year: 1998).*
Wagle et al. (Cancer Discovery, 2012, vol. 2:82-93) (Year: 2012).*
Uitdewilligen et al. (PLoS one, 2013, 8(5):e62355, p. 1-14) (Year: 2013).*
Bergval et al. (PLoS One, 2012, 7(8):e43240; p. 1-16) (Year: 2012).*
Liu et al. (Forensic Sci Intl Genet, 2014, 13, p. 10-19, epub Mar. 2014) (Year: 2014).*
Casas et al., Biotechniques 20:219-25 (1996).
Cheung et al., Proc. Natl. Acad. Sci. USA, 93:14676-79 (1996).
Cockroft, J. Am. Chem. Soc. 130, 818-820 (2008).
Deamer, Trends Biotechnol. 18, 147-151 (2000).
Deamer, Acc. Chem. Res. 35:817-825 (2002).
Dean et al., Proc. Natl. Acad. Sci. USA 99:5261-66 (2002).
Eberle et al. (2016) bioRxiv doi: 10.1101/055541.
Grothues et al. Nucleic Acids Res. 21(5):1321-2 (1993).
Healy, Nanomed. 2, 459-481 (2007).
Kidd, Forensic Sci Int. 2006; 164(1): 20-32.
Kittler et al., Anal. Biochem. 300:237-44 (2002).
Korlach, Proc. Natl. Acad. Sci. USA 105, 1176-1181 (2008).
Lage et al., Genome Research 13:294-307 (2003).
Levene, Science 299, 682-686 (2003).
Li, Nat. Mater. 2:611-615 (2003).
Lizardi et al., Nat. Genet. 19:225-232 (1998).
Lundquist, Opt. Lett. 33, 1026-1028 (2008).
Metzker, Genome Res. 15:1767-1776 (2005).
Ronaghi, (1996), Analytical Biochemistry 242(1), 84-9.
Ronaghi, (1998) Science 281(5375), 363.
Ronaghi, (2001) Genome Res. 11(1), 3-11.
Ruparel et al., Proc Natl Acad Sci USA 102: 5932-7 (2005).
Sanchez, Electrophoresis 2006; 27(9):1713-1724.
Soni, Clin. Chem. 53, 1996-2001 (2007).
Walker et al., Nucl. Acids Res. 20:1691-96 (1992).
Walker et al., Molecular Methods for Virus Detection, Academic Press, Inc., 1995.
Agilent Technologies, SureDirect Blood PCR Kit: Protocol, 2014.
Chacon-Cortes et al., Comparison of genomic DNA extraction techniques from whole blood samples: a time, cost and quality evaluation study, Molecular Biology Reports, An International Journal on Molecular and Cellular Biology, 2012, 39(5), 5961-5966.
Goldenberger et al., A Simple "Universal" DNA Extraction Procedure Using SDS and Proteinase K is Compatible with Direct PCR Amplification, Genome Res. 1995, 368-370.
Kanai et al., Rapid and simple method for preparation of genomic DNA form easily obtainable clotted blood, J. Clinical Pathol. 1994, 47(11), 1043-1044.
April et al., "Whole-Genome Gene Expression Profiling of Formalin-Fixed, Paraffin-Embedded Tissue Samples," PLOS One 2009, 4(12), e8162.
Fedick et al., "High-throughput real-time PCR-based genotyping without DNA purification," BMC Research Notes, Biomed Central LTD, 2012, 5(1), 573.
Herraez-Hernandez et al., "Detection and Genotyping of Human Papillomavirus DNA in Formalin-Fixed Paraffin-Embedded Specimens with the HPV Direct Flow CHIP System," The Open Virology Journal, 2013, 7(1), 91-95.
Bruinsma et al., "Bead-linked transposomes enable a normalization-free workflow for NGS library preparation", BMC Genomics, Biomed Central Ltd., 2018, 19(1), 1-16.
Cawkwell et al., "Direct multiplex amplification of DNA from a formalin fixed, paraffin wax embedded tissue section," J Clin Pathol: Mol Pathol, 2000, 53:51-52.
Dedhia et al., "Evaluation of DNA Extraction Methods and Real Time PCR Optimization on Formalin-fixed Paraffin-embedded Tissues", Asian Pacific Journal of Cancer Prevention, Asian Pacific Organization for Cancer Prevention, 2007, 8(1), 55-59.
Do et al., "Reducing Sequence Artifacts in Amplicon-Based Massively Parallel Sequencing of Formalin-Fixed Paraffin-Embedded DNA by Enzymatic Depletion of Uracil-Containing Templates", Clinical Chemistry, American Association for Clinical Chemistry, 2013, 59(9), 1376-1383.
Do et al., "Sequence Artifacts in DNA from Formalin-Fixed Tissues: Causes and Strategies for Minimization", Clinical Chemistry, 2014, 61(1), 64-71.
Extended Search Report in European Application No. 20165344.1, mailed Jul. 21, 2020.
Search Report in European Application No. 16738505.3, mailed Nov. 15, 2019.
Feijun et al. "Forensic Experiment Guide", Sichuan University Press, 2010.
Lenze et al., "Considerations for the use of formalin-fixed and paraffin-embedded tissue specimens for clonality analysis", Journal of Hematopathology, Springer Berlin Heidelberg, 2012, 5(1), 27-34.
Office Action issued in Chinese Patent Application No. 201580041770.3, dated Nov. 19, 2020.
Sah et al., "Functional DNA quantification guides accurate next-generation sequencing mutation detection in formalin-fixed, paraffin-embedded tumor biopsies", Genome Medicine, 2013, 5(30), 1-12.
Smigielska-Czepiel et al., "Dual Role of miR-21 in CD4+ T-Cells: Activation-Induced miR-21 Supports Survival of Memory T-Cells and Regulates CCR7 Expression in Naïve T-Cells", PLOS One, 2013, 8(10), e76217-e76217.
Written Opinion issued in SG Patent Application No. 11201610315Y, dated Jun. 8, 2019.
Campa, M., "QuickExtract™FFPE DNA Extraction Kit From Epicentre Biotechnologies," www.biocompare.com/Product-Reviews/40517-QuickExtract-FFPE-DNA-Extraction-Kit-From-Epicentre-Biotechnologies/, Jan. 15, 2009.
Park et al., "Detection of Hepatitis C Virus RNA Using Ligation-Dependent Polymerase Chain Reaction in Formalin-Fixed, Paraffin-Embedded Liver Tissues," Am. J. Pathol. 1996, 149(5), 1485-1491.
Park et al., "Direct STR Amplification from Whole Blood and Blood- or Saliva-Spotted FTA without DNA Purification," Journal of Forensic Sciences, 2008, 53(2), 335-341.

(56) References Cited

OTHER PUBLICATIONS

International Search Report and Written Opinion, PCT Appln. No. PCT/GB2016/052026, Sep. 6, 2016, 17 pages.
Zhang et al., "Direct DNA Amplification from Crude Clinical Samples Using a PCR Enhancer Cocktail and Novel Mutants of Taq," Journal of Molecular Diagnostics, 2010, 12(2), 152-161.

* cited by examiner

| dbsnp ID | CS219 gDNA | CS219 spot | CS220 gDNA | CS220 spot | CS221 gDNA | CS221 spot | CS222 gDNA | CS222 spot | CS223 gDNA | CS223 spot | CS224 gDNA | CS224 spot | CS225 gDNA | CS225 spot |
|---|---|---|---|---|---|---|---|---|---|---|---|---|---|---|
| rs2229546 | alt | alt | het | het | ref | ref | alt | alt | het | het | het | het | het | het |
| rs1410592 | ref | ref | ref | ref | alt | alt | alt | het | het | het | het | het | het | het |
| rs497692 | alt | alt | het | het | alt | alt | het | alt | alt | alt | alt | alt | het | het |
| rs10203363 | ref | ref | ref | ref | het | het | het | het | het | het | het | het | ref | ref |
| rs2819561 | alt | alt | alt | alt | het | het | het | het | alt | het | het | alt | alt | alt |
| rs4688963 | ref | ref | ref | ref | het | het | het | het | het | het | het | het | het | het |
| rs309557 | het | het | alt | alt | het | het | ref | ref | het | het | alt | alt | het | het |
| rs2942 | ref | ref | ref | ref | ref | ref | alt | alt | het | het | het | het | het | het |
| rs17548783 | ref | ref | ref | ref | het | het | het | het | het | het | ref | ref | het | het |
| rs4735258 | het | het | alt | alt | alt | alt | alt | alt | alt | alt | alt | alt | ref | ref |
| rs1381532 | alt | alt | het | het | het | het | het | het | het | het | het | het | het | het |
| rs10883099 | het | het | ref | ref | het | het | ref | ref | ref | ref | ref | ref | het | het |
| rs4617548 | het | het | ref | ref | het | het | het | het | het | het | alt | alt | het | het |
| rs7300444 | ref | ref | het | het | het | het | het | het | alt | alt | alt | alt | het | het |
| rs9532292 | alt | alt | alt | alt | alt | alt | het | het | het | het | het | het | het | het |
| rs2297995 | ref | ref | het | het | ref | ref | ref | ref | ref | ref | ref | ref | ref | ref |
| rs4577050 | alt | alt | het | het | het | het | het | het | alt | alt | alt | alt | het | het |
| rs2070203 | ref | ref | het | het | alt | alt | het | het | alt | alt | het | het | het | het |
| rs1037256 | alt | alt | het | het | het | het | het | het | het | het | het | het | het | het |
| rs9962023 | alt | alt | het | het | alt | alt | het | het | ref | ref | ref | ref | het | het |
| rs2228611 | ref | ref | het | het | het | het | het | het | alt | alt | ref | ref | ref | ref |
| rs10373 | het | het | alt | alt | alt | alt | ref | ref | alt | alt | ref | ref | het | het |
| rs4148973 | het | het | het | het | het | het | ref | ref | het | het | het | het | het | het |
| rs4148973 | ref | ref | ref | ref | ref | ref | ref | ref | het | het | het | het | alt | alt |

Fig. 5

SAMPLE PREPARATION FOR NUCLEIC ACID AMPLIFICATION

BACKGROUND

Whole genome sequencing (WGS) is one approach that has application in personalized medicine for identifying disease risks for specific patients, as well as their potential responsiveness to certain therapies (e.g., drug therapy). In a clinical setting, various factors such as complex sample preparation workflows or outsourcing of sample preparation and/or sequencing makes sample mix-ups possible and difficult to detect. One essential condition of a WGS-based approach in clinical applications (e.g., diagnostics, prognostics, and/or therapeutics) is that the sequence information used be unequivocally derived from the specific patient, i.e., ensuring sample identity is essential to allow the accurate assignment of clinical details to sequence data. There is a need for methods of confirming sample identity in WGS data used in clinical applications. There is also a need for sample preparation methods that do not require purification of DNA prior to amplification. Embodiments of the invention set forth herein satisfy these needs and provide other advantages as well.

BRIEF SUMMARY

Presented herein are methods and compositions for targeted amplification of DNA and sample identification. The methods set forth herein are particularly useful, for example, in validation and quality control of samples and to confirm that WGS sequence data is properly paired with a patient sample prior to delivering sequence data to a physician or to a patient. However, it will be appreciated that the methods set forth herein can be used for other suitable applications where quick targeted amplification is desired.

In accordance with the above, in one embodiment presented herein are methods for obtaining nucleic acid sequence information from a biological sample comprising: (a) providing a biological sample comprising different target nucleic acids; (b) contacting the biological sample with a plurality of different probe sets to form hybridization complexes with the different target nucleic acids; (c) amplifying the nucleic acid from the biological samples to produce amplicons; wherein there is no purification of the nucleic acid from the biological sample prior to the contacting step (b); and (d) obtaining nucleic acid sequence information for a plurality of portions of the amplified sample.

In certain aspects, there is no purification of the nucleic acid from the biological sample prior to the amplifying in step (c). In certain aspects, the amplifying in step (c) comprises polymerase chain reaction using at least two amplification primers that are specific for a portion of the sample genome. In certain aspects, the amplifying in step (c) comprises extension and ligation of two probes to form amplification templates.

In certain aspects, the supernatant comprising solution-phase hybridization complexes is further contacted with a solid support to form immobilized hybridization complexes when contacted with the extension enzyme and the nucleotides. In certain aspects, the solid support comprises beads. In certain aspects, the solid support comprises a filter plate.

In certain aspects, each of the different target nucleic acids comprises, from 3' to 5': contiguous first, second, and third target domains and each probe set comprises: (i) a first probe comprising, from 5' to 3': a first priming sequence and a sequence that is substantially complementary to a first target domain; and (ii) a second probe comprising 5' to 3': a sequence substantially complementary to a third target domain, and a second priming sequence.

In certain aspects, the method comprises, prior to step (c), a step of collecting a supernatant comprising solution-phase hybridization complexes from the biological sample. In certain aspects, obtaining nucleic acid sequence information comprises massively parallel sequencing. In certain aspects, obtaining nucleic acid sequence information comprises detecting the amplicons on the surface of a nucleic acid array.

In certain aspects, the plurality of probe set comprises at least at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 different probe sets. In certain aspects, the plurality of probe set comprises a plurality of probes configured to selectively hybridize to polymorphic regions that are informative of the identity of the source of the sample. In certain aspects, the plurality of probe set comprises a plurality of probes configured to selectively hybridize to regions that comprise cancer-associated polymorphisms. In certain aspects, the sample is a human sample. In certain aspects, the sample comprises tumor tissue. In certain aspects, the sample comprises normal tissue. In certain aspects, the sample is a blood sample. In certain aspects, the sample comprises dried blood on a porous solid surface. In certain aspects, the porous solid surface comprises filter paper.

Also presented herein is a method of obtaining nucleic acid sequence information from a FFPE sample comprising: (a) providing a FFPE sample comprising different target nucleic acids embedded within a preserved tissue; (b) contacting the FFPE sample with a plurality of different probe sets to form hybridization complexes with the different target nucleic acids; (c) amplifying the nucleic acid from the FFPE samples to produce amplicons; wherein there is no purification of the nucleic acid from the FFPE sample prior to the contacting step (b); and (d) obtaining nucleic acid sequence information for a plurality of the amplicons. In particular embodiments, there is no purification of the nucleic acid from the FFPE sample prior to the amplifying in step (c).

In certain aspects, the amplifying in step (c) comprises polymerase chain reaction using at least two amplification primers that are specific for a portion of the sample genome. In certain aspects, the amplifying in step (c) comprises extension and ligation of two probes to form amplification templates. In certain aspects, the supernatant comprising solution-phase hybridization complexes is further contacted with a solid support to form immobilized hybridization complexes when contacted with the extension enzyme and the nucleotides.

In certain aspects, the solid support comprises beads. In certain aspects, the solid support comprises a filter plate. In certain aspects, each of the different target nucleic acids comprises, from 3' to 5': contiguous first, second, and third target domains and each probe set comprises: (i) a first probe comprising, from 5' to 3': a first priming sequence and a sequence that is substantially complementary to a first target domain; and (ii) a second probe comprising 5' to 3': a sequence substantially complementary to a third target domain, and a second priming sequence. In certain aspects, the method comprises, prior to step (c), a step of collecting a supernatant comprising solution-phase hybridization complexes from the FFPE sample.

In certain aspects, obtaining nucleic acid sequence information comprises massively parallel sequencing. In certain aspects, obtaining nucleic acid sequence information comprises detecting the amplicons on the surface of a nucleic acid array.

In certain aspects, the plurality of probe set comprises at least at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 different probe sets. In certain aspects, the plurality of probe set comprises a plurality of probes configured to selectively hybridize to polymorphic regions that are informative of the identity of the source of the sample. In certain aspects, the plurality of probe set comprises a plurality of probes configured to selectively hybridize to regions that comprise cancer-associated polymorphisms. In certain aspects, the sample is a human sample. In certain aspects, the sample comprises tumor tissue.

Also presented herein are methods for amplification of nucleic acid from a FFPE sample comprising: (a) providing a FFPE sample comprising nucleic acid embedded within a preserved tissue, the nucleic acid having, from 3' to 5': contiguous first, second, and third target domains; (b) contacting the FFPE sample with a plurality of different probe sets to form hybridization complexes with the different target nucleic acids, wherein each probe set comprises: (i) a first probe comprising, from 5' to 3': a first priming sequence and a sequence that is substantially complementary to the first target domain; and (ii) a second probe comprising 5' to 3': a sequence substantially complementary to the third target domain, and a second priming sequence; (c) contacting the hybridization complexes with an extension enzyme and nucleotides, wherein the first probes are extended along the second target domains of hybridization complexes formed in (b); (d) ligating the extended first probes to the second probes to form amplification templates; and (e) amplifying the amplification templates with first and second primers that are complementary to the first priming sequence and the second priming sequence to produce amplicons and obtaining nucleic acid sequence information for a plurality of the amplicons.

In certain aspects, the method comprises, prior to step (c), a step of collecting a supernatant comprising solution-phase hybridization complexes from the FFPE sample. In certain aspects, the supernatant comprising solution-phase hybridization complexes is further contacted with a solid support to form immobilized hybridization complexes when contacted with the extension enzyme and the nucleotides. In certain aspects, the solid support comprises beads. In certain aspects, the solid support comprises a filter plate. In certain aspects, obtaining nucleic acid sequence information comprises massively parallel sequencing. In certain aspects, obtaining nucleic acid sequence information comprises detecting the amplicons on the surface of a nucleic acid array.

In certain aspects, the plurality of probe set comprises at least at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 different probe sets. In certain aspects, the plurality of probe set comprises a plurality of probes configured to selectively hybridize to polymorphic regions that are informative of the identity of the source of the sample. In certain aspects, the plurality of probe set comprises a plurality of probes configured to selectively hybridize to regions that comprise cancer-associated polymorphisms. In certain aspects, the sample is a human sample. In certain aspects, the sample comprises tumor tissue. In certain aspects, the sample comprises normal tissue.

Also presented herein is a method for nucleic acid sample identification comprising: (a) providing a nucleic acid-containing cellular sample; (b) lysing cells of the sample with a lysis reagent to liberate nucleic acid from within the cells of the cellular sample, thereby forming a lysate; (c) amplifying the nucleic acid from the lysed samples; wherein there is no purification of the nucleic acid from the lysate prior to beginning the amplification step (c); and (d) obtaining nucleic acid sequence information for a plurality of portions of the amplified sample, and comparing the sequence information to a second set of sequence information.

In certain aspects, the nucleic acid is DNA. In certain aspects, the sample is a blood sample. In certain aspects, the sample comprises dried blood. In certain aspects, the sample comprises a FFPE tissue sample. In certain aspects, the second set of sequence information comprises a whole genome sequence. In certain aspects, the second set of sequence information comprises exome sequence information.

In certain aspects, the amplifying comprises a targeted amplification reaction. In certain aspects, the targeted amplification reaction comprises extension and ligation of two probes. In certain aspects, the targeted amplification reaction comprises polymerase chain reaction using at least two amplification primers that are specific for a portion of the sample genome.

Also presented herein is a method of tracking the identity of a biological sample during different stages of sample processing, comprising: (a) providing a nucleic acid-containing cellular sample; (b) separating a portion of the sample into a first portion and a second portion and obtaining a first set of nucleic acid sequence information from the first portion the biological sample according to any of the embodiments presented herein, wherein the first set of nucleic acid sequence information comprises identity informative sequence information; (c) purifying nucleic acid from the second portion and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same source.

In certain aspects, the identity informative sequence information comprises SNP genotype information for at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 unique SNPs. In certain aspects, the second set of sequence information comprises SNP genotype information for at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 unique SNPs.

In certain aspects, the nucleic acid is DNA. In certain aspects, the sample is a blood sample. In certain aspects, the sample comprises dried blood. In certain aspects, the sample comprises dried blood on a porous solid surface. In certain aspects, the sample comprises a FFPE tissue sample. In certain aspects, the second set of sequence information comprises a whole genome sequence. In certain aspects, the second set of sequence information comprises exome sequence information.

Also presented herein is a method of confirming the source of two different biological samples comprising: (a) providing a first nucleic acid-containing cellular sample; (b) obtaining a first set of nucleic acid sequence information from the first portion the biological sample according to any of the embodiments presented herein, wherein the first set of nucleic acid sequence information comprises identity informative sequence information; (c) providing a second nucleic acid sample comprising purified nucleic acid and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same individual.

In certain aspects, the identity informative sequence information comprises SNP genotype information for at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 unique SNPs. In certain aspects, the second set of sequence information comprises SNP genotype information for at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 unique SNPs.

In certain aspects, the nucleic acid is DNA. In certain aspects, the sample is a blood sample. In certain aspects, the sample comprises dried blood. In certain aspects, the sample comprises dried blood on a porous solid surface. In certain aspects, the sample comprises a FFPE tissue sample. In certain aspects, the second set of sequence information comprises a whole genome sequence. In certain aspects, the second set of sequence information comprises exome sequence information.

The details of one or more embodiments are set forth in the accompanying drawings and the description below. Other features, objects, and advantages will be apparent from the description and drawings, and from the claims.

Additional embodiments can be found in U.S. Provisional Patent Application No. 61/189,063 filed on Jul. 6, 2015, the contents of which are incorporated herein by reference in their entireties.

BRIEF DESCRIPTION OF THE DRAWINGS

FIG. 5 shows a table of the SNP calls for 7 donor samples (i.e., CS219, CS220, CS221, CS222, CS223, CS224, and CS225) of Table 2 for both genomic DNA (gDNA) and DBS sample ("spot").

DETAILED DESCRIPTION

Figure 1:
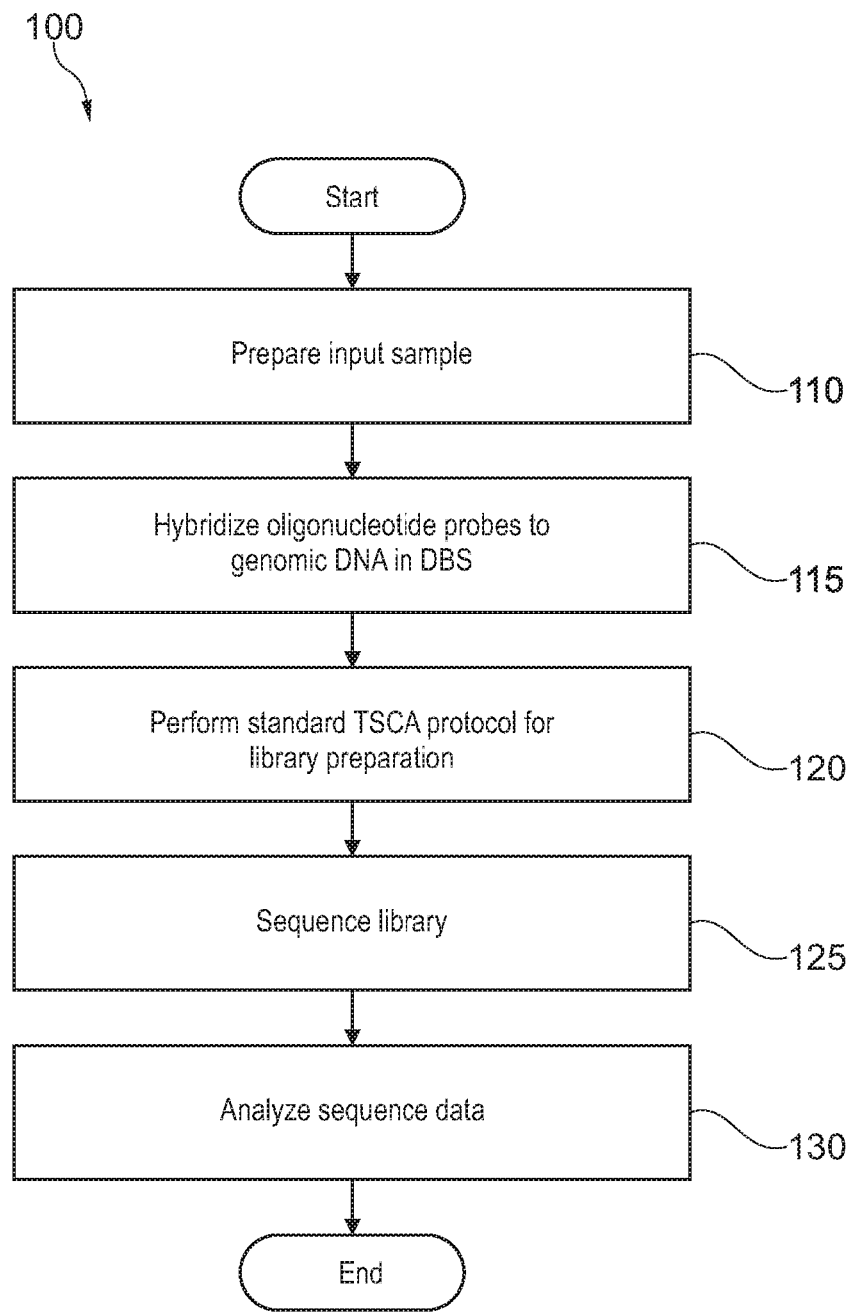
FIG. 1 illustrates a flow diagram of an example of method of using TruSeq® Custom Amplicon for preparation of targeted amplicon libraries and subsequent sequencing for sample identification.

The present disclosure provides methods for targeted amplification of DNA and sample identification. The methods set forth herein are particularly useful, for example, in validation and quality control of samples and to confirm that WGS sequence data is properly paired with a patient sample prior to delivering sequence data to a physician or to a patient. However, it will be appreciated that the methods set forth herein can be used for other suitable applications where quick targeted amplification is desired.

In some embodiments, the present disclosure relates to methods for preparing samples for subsequent nucleic acid (e.g. DNA) amplification, which methods are simpler to perform than existing methods. In particular, the present invention relates to methods wherein purifying nucleic acid (e.g. DNA) from a sample is not required prior to amplification.

The methods set forth herein are particularly useful, for example, in validation and quality control of samples and to confirm that WGS sequence data is properly paired with a patient sample prior to delivering sequence data to a physician or to a patient. However, it will be appreciated that the methods set forth herein can be used for other suitable applications where quick targeted amplification is desired.

Accordingly, in some embodiment presented herein are methods for obtaining nucleic acid sequence information from a biological sample comprising: (a) providing a biological sample comprising different target nucleic acids; (b) contacting the biological sample with a plurality of different probe sets to form hybridization complexes with the different target nucleic acids; (c) amplifying the nucleic acid from the biological samples to produce amplicons; wherein there is no purification of the nucleic acid from the biological sample prior to the contacting step (b); and (d) obtaining nucleic acid sequence information for a plurality of portions of the amplified sample.

In some of the above embodiments, there is no purification of the nucleic acid from the biological sample prior to the amplifying in step (c). Instead, amplification takes place in the presence of the components of the sample, including cellular debris and material used for storage of the biological sample. For example, in some embodiments, the amplification reaction takes place in the presence of formalin and paraffin components, in addition to cellular debris. In certain aspects, the amplifying in step (c) comprises polymerase chain reaction using at least two amplification primers that are specific for a portion of the sample genome. In certain aspects, the amplifying in step (c) comprises extension and ligation of two probes to form amplification templates.

In certain aspects, the supernatant comprising solution-phase hybridization complexes is further contacted with a solid support to form immobilized hybridization complexes when contacted with the extension enzyme and the nucleotides. For example, the solid support can be beads, particles, a filter plate, and the like.

In certain aspects, each of the different target nucleic acids comprises, from 3' to 5': contiguous first, second, and third target domains and each probe set comprises: (i) a first probe comprising, from 5' to 3': a first priming sequence and a sequence that is substantially complementary to a first target domain; and (ii) a second probe comprising 5' to 3': a sequence substantially complementary to a third target domain, and a second priming sequence.

In certain aspects, the method comprises, prior to the amplifying step, a step of collecting a supernatant comprising solution-phase hybridization complexes from the biological sample. In certain aspects, obtaining nucleic acid sequence information comprises massively parallel sequencing. In certain aspects, obtaining nucleic acid sequence information comprises detecting the amplicons on the surface of a nucleic acid array.

In some embodiments presented herein, the method is a method of obtaining nucleic acid sequence information from a FFPE sample comprising: (a) providing a FFPE sample comprising different target nucleic acids embedded within a preserved tissue; (b) contacting the FFPE sample with a plurality of different probe sets to form hybridization complexes with the different target nucleic acids; (c) amplifying the nucleic acid from the FFPE samples to produce amplicons; wherein there is no purification of the nucleic acid from the FFPE sample prior to the contacting step (b); and (d) obtaining nucleic acid sequence information for a plurality of the amplicons. In particular embodiments, there is no purification of the nucleic acid from the FFPE sample prior to the amplifying in step (c).

In some embodiments are methods for amplification of nucleic acid from a FFPE sample comprising: (a) providing a FFPE sample comprising nucleic acid embedded within a preserved tissue, the nucleic acid having, from 3' to 5': contiguous first, second, and third target domains; (b) contacting the FFPE sample with a plurality of different probe sets to form hybridization complexes with the different target nucleic acids, wherein each probe set comprises: (i) a first probe comprising, from 5' to 3': a first priming sequence and a sequence that is substantially complementary to the first target domain; and (ii) a second probe comprising 5' to 3': a sequence substantially complementary to the third target domain, and a second priming sequence; (c) contacting the hybridization complexes with an extension enzyme and nucleotides, wherein the first probes are extended along the second target domains of hybridization complexes formed in (b); (d) ligating the extended first probes to the second probes to form amplification templates; and (e) amplifying the amplification templates with first and second primers that are complementary to the first priming sequence and the second priming sequence to produce amplicons and obtaining nucleic acid sequence information for a plurality of the amplicons.

In certain aspects, the method comprises, prior to step (c), a step of collecting a supernatant comprising solution-phase hybridization complexes from the FFPE sample. In certain aspects, the supernatant comprising solution-phase hybridization complexes is further contacted with a solid support to form immobilized hybridization complexes when contacted with the extension enzyme and the nucleotides. In certain aspects, the solid support comprises beads. In certain aspects, the solid support comprises a filter plate. In certain aspects, obtaining nucleic acid sequence information comprises massively parallel sequencing. In certain aspects, obtaining nucleic acid sequence information comprises detecting the amplicons on the surface of a nucleic acid array.

In some embodiments presented herein, the method is a method for nucleic acid sample identification comprising: (a) providing a nucleic acid-containing cellular sample; (b) lysing cells of the sample with a lysis reagent to liberate nucleic acid from within the cells of the cellular sample, thereby forming a lysate; (c) amplifying the nucleic acid from the lysed samples; wherein there is no purification of the nucleic acid from the lysate prior to beginning the amplification step (c); and (d) obtaining nucleic acid sequence information for a plurality of portions of the amplified sample, and comparing the sequence information to a second set of sequence information.

As used herein, "targeted amplification" can refer to any amplification method used to amplify target nucleic acid sequences of interest. In some embodiments, the targeted amplification can include amplicon preparation and sequencing on a solid support, as set forth in any one of the disclosures of PCT/US2014/071263, filed on Dec. 18, 2014, entitled "AMPLICON PREPARATION AND SEQUENCING ON SOLID SUPPORTS" and PCT/EP2014/079145, filed on Dec. 23, 2014, entitled "POLYNUCLEOTIDE MODIFICATION ON SOLID SUPPORTS", which are incorporated herein by reference in their entireties.

In some embodiments, targeted amplification can comprise hybridization of two or more probes to the same strand of a target nucleic acid sequence of interest, followed by extension of the 3' end of one of the probes and ligation of the extended probe to the other probe, as set forth generally in the materials of U.S. Pat. Nos. 7,803,537, 8,003,354, and 8,906,626, the disclosures of which are incorporated herein by reference in their entireties.

In some embodiments, nucleic acid preparation and amplification is performed without purification of nucleic acid prior to amplification. Some methods of nucleic acid preparation and amplification which are useful in the methods described herein can be found in the disclosures of PCT/GB2015/051674, filed Jun. 9, 2015, entitled "SAMPLE PREPARATION FOR NUCLEIC ACID AMPLIFICATION" and U.S. Application Ser. No. 62/167,463, filed on May 28, 2015, entitled "SURFACE-BASED TAGMENTATION", which are incorporated herein by reference in their entireties.

As used herein, a nucleic acid sample can by any sample comprising nucleic acid. The nucleic acid may be, for example, DNA or RNA. In some embodiments, the sample comprises whole cells, lysed cells, cellular components, or any mixture thereof. In some embodiments, the sample is a blood sample. In some embodiments, the sample is a whole blood sample. Suitable samples can be obtained from tissue, bodily fluid, and/or any other nucleic-acid comprising specimen. In some embodiments, the invention provides methods of preparing non-blood samples, such as tissue samples (e.g. formalin fixed paraffin-embedded (FFPE) samples) for DNA amplification. Such tissue samples may be tumor samples. Other samples may be biopsies, or aspirates, and the like.

The present disclosure provides methods of validating the identity of a DNA sample in genetic testing assay. In one example, the genetic testing assay is a multiplexed whole genome sequencing (WGS) diagnostic assay. In various embodiments, the methods of the invention use sequencing of targeted amplicon libraries to confirm the identity of a sample in a genetic testing assay.

In some embodiments, the targeted amplicon library is prepared using a panel of probes or primers that can be used to selectively amplify a plurality of genomic regions that, alone or in combination, provide information about the identity of the sample. For example, in some embodiments, the panel of probes or primers are used to distinguish the identity of one sample from other samples. In some embodiments, the panel of probes or primers are used to identify a human from which a sample was obtained. In some embodiments, the human can be distinguished from a plurality of other humans. In some embodiments, the human can be uniquely identified. For example, in some embodiments, a panel of probes or primers is used to selectively amplify a plurality of genomic regions that, alone or in combination, uniquely identify the biological source, such as a human donor, from more than 10, 100, 1000, $10^4$, $10^5$, $10^6$, $10^7$, $10^8$, $10^9$, $10^{10}$, or more than $10^{11}$ other human donors. In some embodiments, a panel of probes or primers is used to selectively amplify a plurality of genomic regions that, alone or in combination, uniquely identify the biological source, such as a human donor, from $10^8$, $10^9$, $10^{10}$, more than $10^{11}$ other human donors. As used herein, the term uniquely identify refers to the ability of one or more markers that, alone or in combination, distinguish one particular sample from any other sample.

In some embodiments, the targeted amplicon libraries are prepared using a panel of probes or primers that selectively amplify polymorphic regions. Any polymorphic region may be used in the panels presented herein. For example, in some embodiments, the polymorphic regions are single nucleotide polymorphisms (SNPs). In some embodiments, the polymorphic regions are repeated regions, such as short tandem repeats (STRs). In some embodiments, the panel selectively amplifies a panel that includes a combination of different types of polymorphic regions, such as, for example, a combination of one or more SNPs and one or more STRs.

Any suitable combination of polymorphic regions, and any suitable number of polymorphic regions that provides a desired level of distinction between individuals can be used. In some embodiments, the targeted amplicon libraries are prepared using a panel of probes or primers for detection of identity-informative single nucleotide polymorphisms (iiSNPs), also referred to herein as identity SNPs. Any suitable panel of identity SNPs, as are known in the art, may be used in the methods presented herein, such as, for example, those as described in the disclosures of Kidd K K, et al. Forensic Sci Int. 2006; 164(1): 20-32, and by Sanchez J J, et al. Electrophoresis 2006; 27(9):1713-1724, the disclosure of each of which is incorporated herein by reference in its entirety. In some embodiments, such as those described in examples presented hereinbelow, a panel such as the 45-plex ID SNP subset from ForenSeq set (Illumina, Inc.) may be used in the methods presented herein.

In some embodiments, the identity SNPs are used to discriminate between samples in a multiplex genetic testing assay. The content of an identity SNP panel and/or the number of SNPs in a panel may be selected for a specific application. Primer design (e.g., primer position) for generation of SNP amplicon libraries may be selected for rapid library sequencing. In some embodiments, the SNP panel comprises at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 70, 80, 90, or at least 100 unique SNPs for positive identification of the sample from one or more samples. In some embodiments, the SNP panel comprises at least 19 different SNPs. In some embodiments, the SNP panel comprises at least 52 different SNPs. In one example, an identity SNP panel includes 24 different SNPs. In another example, an identity SNP panel includes 45 different SNPs.

In accordance with the above, in some embodiments, the method comprises contacting a nucleic acid sample with a plurality of different primers of probes configured to selectively amplify a desired panel of polymorphic regions, such as, for example, a combination of one or more SNPs and/or one or more STRs.

By way of a non-limiting example, the panel can comprise one or more of the identity informative SNPs set forth in Table 1 below, in any combination.

TABLE 1

| | | Identity Informative SNPs | | | |
|---|---|---|---|---|---|
| Locus | Amplicon Length (bp) | Chromosome | Amplicon Start Position | Amplicon End Position | 2800M Control Alleles |
| rs10495407 | 109 | 1 | 238439234 | 238439342 | G |
| rs1294331 | 85 | 1 | 233448359 | 233448443 | GA |
| rs1413212 | 64 | 1 | 242806767 | 242806830 | G |

TABLE 1-continued

Identity Informative SNPs

| Locus | Amplicon Length (bp) | Chromosome | Amplicon Start Position | Amplicon End Position | 2800M Control Alleles |
|---|---|---|---|---|---|
| rs1490413 | 98 | 1 | 4367256 | 4367353 | A |
| rs560681 | 90 | 1 | 160786641 | 160786730 | AG |
| rs891700 | 115 | 1 | 239881850 | 239881964 | AG |
| rs1109037 | 118 | 2 | 10085691 | 10085808 | G |
| rs12997453 | 100 | 2 | 182413195 | 182413294 | A |
| rs876724 | 119 | 2 | 114945 | 115063 | C |
| rs907100 | 115 | 2 | 239563542 | 239563656 | CG |
| rs993934 | 120 | 2 | 124109120 | 124109239 | C |
| rs1355366 | 119 | 3 | 190806041 | 190806159 | AG |
| rs1357617 | 120 | 3 | 961696 | 961815 | AT |
| rs2399332 | 157 | 3 | 110300999 | 110301155 | AC |
| rs4364205 | 98 | 3 | 32417576 | 32417673 | G |
| rs6444724 | 120 | 3 | 193207306 | 193207425 | T |
| rs1979255 | 102 | 4 | 190318007 | 190318108 | G |
| rs2046361 | 120 | 4 | 10968994 | 10969113 | A |
| rs279844 | 167 | 4 | 46329584 | 46329750 | AT |
| rs6811238 | 120 | 4 | 169663541 | 169663660 | G |
| rs13182883 | 169 | 5 | 136633252 | 136633420 | AG |
| rs159606 | 104 | 5 | 17374845 | 17374948 | A |
| rs251934 | 97 | 5 | 174778619 | 174778715 | T |
| rs338882 | 157 | 5 | 178690599 | 178690755 | C |
| rs717302 | 110 | 5 | 2879333 | 2879442 | G |
| rs13218440 | 170 | 6 | 12059928 | 12060097 | AG |
| rs1336071 | 120 | 6 | 94537182 | 94537301 | G |
| rs214955 | 120 | 6 | 152697629 | 152697748 | G |
| rs727811 | 115 | 6 | 165045254 | 165045368 | A |
| rs321198 | 165 | 7 | 137029715 | 137029879 | T |
| rs6955448 | 120 | 7 | 4310285 | 4310404 | CT |
| rs737681 | 120 | 7 | 155990742 | 155990861 | T |
| rs917118 | 109 | 7 | 4456953 | 4457061 | C |
| rs10092491 | 116 | 8 | 28411037 | 28411152 | CT |
| rs2056277 | 104 | 8 | 139399038 | 139399141 | C |
| rs4606077 | 151 | 8 | 144656710 | 144656860 | CT |
| rs763869 | 85 | 8 | 1375576 | 1375660 | CT |
| rs1015250 | 117 | 9 | 1823702 | 1823818 | C |
| rs10776839 | 103 | 9 | 137417271 | 137417373 | G |
| rs1360288 | 119 | 9 | 128967994 | 128968112 | C |
| rs1463729 | 99 | 9 | 126881396 | 126881494 | GA |
| rs7041158 | 115 | 9 | 27985907 | 27986021 | C |
| rs3780962 | 94 | 10 | 17193284 | 17193377 | T |
| rs735155 | 170 | 10 | 3374133 | 3374302 | A |
| rs740598 | 120 | 10 | 118506839 | 118506958 | AG |
| rs826472 | 153 | 10 | 2406511 | 2406663 | T |
| rs964681 | 105 | 10 | 132698394 | 132698498 | CT |
| rs10488710 | 118 | 11 | 115207134 | 115207251 | CG |
| rs1498553 | 111 | 11 | 5708981 | 5709091 | CT |
| rs2076848 | 118 | 11 | 134667502 | 134667619 | AT |
| rs901398 | 90 | 11 | 11096173 | 11096262 | T |
| rs10773760 | 99 | 12 | 130761623 | 130761721 | AG |
| rs2107612 | 103 | 12 | 888262 | 888364 | AG |
| rs2111980 | 94 | 12 | 106328186 | 106328279 | G |
| rs2269355 | 65 | 12 | 6945881 | 6945945 | C |
| rs2920816 | 157 | 12 | 40862976 | 40863132 | T |
| rs1058083 | 76 | 13 | 100038193 | 100038268 | AG |
| rs1335873 | 109 | 13 | 20901665 | 20901773 | T |
| rs1886510 | 116 | 13 | 22374646 | 22374761 | CT |
| rs354439 | 170 | 13 | 106938320 | 106938489 | T |
| rs1454361 | 118 | 14 | 25850765 | 25850882 | AT |
| rs4530059 | 170 | 14 | 104769099 | 104769268 | G |
| rs722290 | 101 | 14 | 53216686 | 53216786 | G |
| rs873196 | 114 | 14 | 98845506 | 98845619 | CT |
| rs1528460 | 115 | 15 | 55210664 | 55210778 | T |
| rs1821380 | 118 | 15 | 39313343 | 39313460 | G |
| rs8037429 | 63 | 15 | 53616876 | 53616938 | T |
| rs1382387 | 89 | 16 | 80106318 | 80106406 | GT |
| rs2342747 | 104 | 16 | 5868645 | 5868748 | AG |
| rs430046 | 119 | 16 | 78016980 | 78017098 | C |
| rs729172 | 104 | 16 | 5606153 | 5606256 | C |
| rs740910 | 113 | 17 | 5706552 | 5706664 | A |
| rs8078417 | 143 | 17 | 80461847 | 80461989 | CT |
| rs938283 | 98 | 17 | 77468433 | 77468530 | T |
| rs9905977 | 170 | 17 | 2919324 | 2919493 | G |
| rs1024116 | 93 | 18 | 75432317 | 75432414 | A |
| rs1493232 | 75 | 18 | 1127945 | 1128019 | A |

TABLE 1-continued

Identity Informative SNPs

| Locus | Amplicon Length (bp) | Chromosome | Amplicon Start Position | Amplicon End Position | 2800M Control Alleles |
|---|---|---|---|---|---|
| rs1736442 | 153 | 18 | 55225698 | 55225850 | G |
| rs9951171 | 119 | 18 | 9749789 | 9749907 | G |
| rs576261 | 76 | 19 | 39559780 | 39559855 | AC |
| rs719366 | 170 | 19 | 28463281 | 28463450 | T |
| rs1005533 | 158 | 20 | 39487066 | 39487223 | A |
| rs1031825 | 126 | 20 | 4447416 | 4447541 | C |
| rs1523537 | 117 | 20 | 51296076 | 51296192 | C |
| rs445251 | 119 | 20 | 15124865 | 15124983 | CG |
| rs221956 | 97 | 21 | 43606933 | 43607029 | C |
| rs2830795 | 114 | 21 | 28608089 | 28608202 | A |
| rs2831700 | 79 | 21 | 29679639 | 29679717 | A |
| rs722098 | 101 | 21 | 16685561 | 16685661 | AG |
| rs914165 | 156 | 21 | 42415865 | 42416020 | AG |
| rs1028528 | 78 | 22 | 48362256 | 48362333 | AG |
| rs2040411 | 68 | 22 | 47836378 | 47836445 | A |
| rs733164 | 120 | 22 | 27816711 | 27816830 | AG |
| rs987640 | 120 | 22 | 33559450 | 33559569 | AT |

A sample in a genetic testing assay may be any sample that comprises nucleic acid, such as a biological sample. Non-limiting examples of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, free floating nucleic acids, peritoneal fluid, and pleural fluid, or cells therefrom. Biological samples may also include sections of tissues such as frozen or fixed sections taken for histological purposes or microdissected cells or extracellular parts thereof. In some embodiments, the sample can be a blood sample, such as, for example, a whole blood sample. In another example, the sample is an unprocessed dried blood spot (DBS) sample. In yet another example, the sample is a formalin-fixed paraffin-embedded (FFPE) sample. In yet another example, the sample is a saliva sample. In yet another example, the sample is a dried saliva spot (DSS) sample.

In some embodiments, a panel of identity markers is included in a panel designed to screen for a disease, such as, for example a somatic cancer mutation. As a result, the results of sequencing the combined panels not only provides information about the disease state, but also provides information about the identity of the individual from which the sample was obtained. The combination of disease-informative sequence information and identity-informative sequence information allows the sequence information about the disease to be tied to the identity of the individual. This provides significant advantages in storing and management of sequence data from individuals because the identity informative sequence information is a component of the sequence information obtained when screening for the disease state. Additionally, the identity informative sequence information can be advantageous when comparing the results of the disease screen with other sequence information, such as whole genome sequence information, exome sequence information, or a panel of sequence information that is directed to another disease screen.

In some embodiments, the methods and compositions presented herein allow for tracking the identity of a biological sample during different stages of sample processing. For example, a method of tracking can comprise: (a) providing a nucleic acid-containing cellular sample; (b) separating a portion of the sample into a first portion and a second portion and obtaining a first set of nucleic acid sequence information from the first portion the biological sample according to any of the embodiments presented herein, wherein the first set of nucleic acid sequence information comprises identity informative sequence information; (c) purifying nucleic acid from the second portion and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same source.

In some embodiments, it may be desired to confirm the identity of the source of two different samples. For example, one method can comprise: (a) providing a first nucleic acid-containing cellular sample; (b) obtaining a first set of nucleic acid sequence information from the first portion the biological sample according to any of the embodiments presented herein, wherein the first set of nucleic acid sequence information comprises identity informative sequence information; (c) providing a second nucleic acid sample comprising purified nucleic acid and obtaining a second set of sequence information; and (d) using computer-assisted logic, comparing the identity informative sequence information from the first set of nucleic acid sequence information sequence information to the second set of sequence information to confirm that the first and second sets of sequence information were obtained from the same individual.

Selectively Amplifying

In embodiments presented herein, a panel of target nucleic acids is selectively amplified from a sample. In some embodiments, selectively amplifying can include one or more non-selective amplification steps. For example, an amplification process using random or degenerate primers can be followed by one or more cycles of amplification using target-specific primers.

In one embodiment, the methods of the invention use TruSeq® Custom Amplicon (TSCA) (Illumina, Inc.) for preparation of targeted amplicon libraries for subsequent sequencing and sample validation. The TSCA library preparation protocol uses target specific oligonucleotide probes and a ligation/extension reaction to generate targeted amplicons. For example, in some embodiments, the method can comprise (a) providing a sample having the different target nucleic acids comprising DNA, wherein each nucleic acid comprises, from 3' to 5': contiguous first, second, and third target domains; (b) contacting the sample with a plurality of at least 100 different probe sets to form hybridization complexes with the different target nucleic acids, wherein each probe set comprises: (i) a first probe comprising, from 5' to 3': a first priming sequence and a sequence that is substantially complementary to the first target domain; and (ii) a second probe comprising 5' to 3': a sequence substantially complementary to the third target domain, and a second priming sequence, wherein at least one probe in each of the different probe sets contains a distinct adapter sequence not native to the target nucleic acid; (c) contacting the hybridization complexes with an extension enzyme and nucleotides, wherein the first probes are extended along the second target domains of hybridization complexes formed in (b), wherein the hybridization complexes are immobilized on a solid support when contacted with the extension enzyme and the nucleotides; (d) ligating the extended first probes to the second probes to form amplification templates; (e) amplifying the amplification templates with first and second primers that are complementary to the first priming sequence and the second priming sequence to produce amplicons; and (f) detecting the amplicons on the surface of a nucleic acid array that is different from the solid support that is immobilized to the hybridization complexes.

In another embodiment, the methods of the invention use targeted multiplex PCR amplification for preparation of amplicon libraries for subsequent sequencing and sample validation. Although TSCA and targeted multiplex PCR are described herein as exemplary embodiments, it will be appreciated by one of skill in the art that any of a number of known methodologies for selective capture and/or selective amplification can be used in the methods presented herein for preparation of an amplicon library for subsequent sequencing and sample validation.

As used herein, the terms "amplifying," "amplify," "amplification" and like terms refer to producing one or more copies of a single stranded or double stranded nucleic acid, or a portion thereof. In some embodiments, the methods provided herein can include a step of producing an amplified nucleic acid under isothermal or thermal variable conditions.

As used herein the terms "selectively" and "targeted" and the like, when used in reference to "amplifying" "amplification" (or grammatical equivalents), refers to preferentially amplifying a first nucleic acid in a sample compared to one or more other nucleic acids in the sample. The term can refer to producing one or more copies of the first nucleic acid and substantially no copies of the other nucleic acids. The term can also refer to producing a detectable amount of copies of the first nucleic acid and an undetectable (or insignificant) amount of copies of the other nucleic acids under a particular detection condition used.

Any suitable amplification methodology can be utilized to selectively or non-selectively amplify one or more nucleic acid molecules from an individual according to the methods and systems presented herein. It will be appreciated that any of the amplification methodologies described herein or generally known in the art can be utilized with target-specific primers to selectively amplify a nucleic acid molecule of interest. Suitable methods for selective amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to selectively amplify one or more nucleic acids of interest. For example, PCR, including multiplex PCR, SDA, TMA, NASBA and the like can be utilized to selectively amplify one or more nucleic acids of interest. In such embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to selectively amplify a target nucleic acid of interest. For example, in some embodiments, the selective amplification method can include ligation probe amplification or oligonucleotide ligation assay (OLA) reactions that contain primers directed specifically to the nucleic acid of interest. In some embodiments, the selective amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, CA).

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo⁻ for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

A further approach that can be used to amplify gDNA in connection with the methods of the present disclosure is degenerate oligonucleotide primed polymerase chain reaction (DOP-PCR) under conditions such as, but not limited to, those described by Cheung et al., Proc. Natl. Acad. Sci. USA, 93:14676-79 (1996) or U.S. Pat. No. 5,043,272, the disclosures of which are incorporated herein by reference in their entireties. Low amounts of gDNA, for example, 15 pg of human gDNA, can be amplified to levels that are conveniently detected in the methods of the present disclosure. Reaction conditions used in the methods of Cheung et al. can be selected for production of an amplified representative population of genome fragments having near complete coverage of the human genome. Furthermore modified versions of DOP-PCR, such as those described by Kittler et al. in a protocol known as LL-DOP-PCR (Long products from Low DNA quantities-DOP-PCR) can be used to amplify gDNA in accordance with the present disclosure (Kittler et al., Anal. Biochem. 300:237-44 (2002), the disclosure of which is incorporated herein by reference in its entirety).

Primer-extension preamplification polymerase chain reaction (PEP-PCR) can also be used in a method of the present disclosure in order to amplify gDNA. Useful conditions for amplification of gDNA using PEP-PCR include, for example, those described in Casas et al., Biotechniques 20:219-25 (1996), incorporated herein by reference in its entirety.

In some embodiments, selective amplification can include a method to pull-down a nucleic acid of interest from a mixture of different nucleic acids. The pull-down can occur prior to or after amplification occurs. Pull-down methods are well known in the art, and can include, for example, nucleic acid pull-down using biotinylated probes or arrays of probes.

The present methods are not limited to any particular amplification technique and amplification techniques described herein are exemplary only with regards to methods and embodiments of the present disclosure.

The methods of the invention provide for a rapid test using "raw" sample input (e.g., unprocessed dried blood spot) and/or processed sample input (e.g., purified genomic DNA) that may be used to quickly and unequivocally confirm sample identity of WGS data.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057,026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/0270305 and U.S. Patent Pub. No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 2013/0079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Pub. No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm2, 100 features/cm2, 500 features/cm2, 1,000 features/cm2, 5,000 features/cm2, 10,000 features/cm2, 50,000 features/cm2, 100,000 features/cm2, 1,000,000 features/cm2, 5,000,000 features/cm2, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. patent application Ser. No. 13/273,666, which is incorporated herein by reference.

TSCA Library Preparation and Sequencing for Sample Validation

In one embodiment, the methods of the invention use the TruSeq® Custom Amplicon (referred to herein as "TSCA") for preparation of targeted amplicon libraries for subsequent sequencing and sample identification.

FIG. 1 illustrates a flow diagram of an example of a method 100 of using TruSeq® Custom Amplicon for preparation of targeted amplicon libraries and subsequent sequencing for sample identification. In this example, TruSeq® Custom Amplicon v1 is used. Method 100 includes, but is not limited to, the following steps.

At a step 110, an input sample is prepared. In one example, the input sample is a 3 mm punch from a DBS sample. In one embodiment, the DBS punch is placed directly in a well of a 96-well plate or other suitable reaction vessel such as a microcentrifuge tube or the like. In some embodiments, the punch is undergoes further manipulations, such as rinsing, soaking, incubating, or shaking, to process the sample material and prepare it for downstream library preparation steps. For example, the sample may be placed in a buffer for a suitable amount of time to allow further permeabilization of the sample material and free up the nucleic acid for better access to hybridization and amplification reagents. In some embodiments the sample is a punch from a blood spot. In some embodiments, the sample comprises FFPE.

At a step 115, a pool of upstream and downstream oligonucleotides specific to targeted SNPs is hybridized to genomic DNA on the DBS sample punch. In one example, the panel of oligonucleotide includes upstream and downstream oligonucleotides targeting 24 identity-informative SNPs. For example, an aliquot of the oligonucleotide pool and an aliquot of hybridization buffer are added directly to each well containing a DBS sample punch. The 96-well plate is placed on a heating block heated to about 96° C., incubated for about 1 minute, and then the temperature is slowly cooled to about 40° C. (e.g., slowly cooled over about 2 hours). At the end of the hybridization incubation, the supernatant is removed from each well (leaving the DBS punch in the well) and transferred to a new 96-well plate.

At a step 120, the standard steps in the TSCA protocol for library preparation are performed (e.g., removal of unbound oligonucleotides, extension/ligation of bound oligonucleotides, PCR amplification of extension-ligation products, etc.). In one example, removal of unbound oligonucleotide is performed using a filter plate (i.e., TSCA v1).

At a step 125, an aliquot of the amplified DBS library samples are pooled and sequenced. Any one of a number of known sequencing methodologies as described hereinabove can be used to sequence the library. In some embodiments, the pooled library samples are sequenced using massively parallel sequencing, for example, on a MiSeq version 3 instrument (Illumina, Inc.)

At a step 130, the sequencing data is analyzed. For example, the sequencing data is analyzed using MiSeq Reporter tool using Smith-Waterman aligner and GATK variant calling at the 24 SNP positions.

In another example (not shown), a TruSeq® Custom Amplicon protocol that includes a bead-based process for removal of unbound oligonucleotides (i.e., TSCA v2) is used to prepare targeted amplicon libraries for sequencing and sample identification.

To evaluate method 100 of FIG. 1, blood samples from 10 healthy donors were used. The blood samples were purchased from Clinical Trials Laboratory Service. Upon receipt of each sample, dried blood spot samples were prepared by applying an aliquot (e.g., about 50 μl to about 70 μL) of each blood sample on individual filter paper cards (i.e., Guthrie cards) and drying the sample on the card. Table 2 below shows a list of the donor samples that were used to evaluate method 100 of FIG. 1. Each sample is designated by a CS number, e.g., CS212, CS219, CS220, etc. Italicized CS numbers, i.e., CS219, CS224, and CS308 are blood samples from the same individual (i.e., Patient ID KD241283) provided at different time points and used as a reference individual. All blood spots were less than 6 months old ("Date of blood arrival"). All blood samples were within a "normal" range (e.g., 3,000-10,000/μL in healthy individuals) for white blood cell counts ("WBC count") although the WBC counts differ between samples. For some donor blood samples, genomic DNA (indicated by "x" in "DNA stored" column) was also isolated from the blood sample using a QiaAmp kit and extraction protocol (available from Qiagen). Genomic DNA was used as a comparative control for library preparation and SNP calling.

TABLE 2

Donor blood samples Blood Spots

| CS Number | Patient ID | Date of blood arrival | WBC count (×10^9/L) | Blood stored at −80° C. | gDNA extracted |
|---|---|---|---|---|---|
| CS212 | DP090486 | 16/12/2014 | 13.9 | — | — |
| *CS219* | *KD241283* | *14/01/2015* | *9.14* | *x* | *x* |
| CS220 | B1070293 | 20/01/2015 | 7.22 | x | x |
| CS221 | VP180886 | 20/01/2015 | 6.06 | x | x |
| CS222 | RR310794 | 20/01/2015 | 6.57 | x | x |
| CS223 | KK150693 | 20/01/2015 | 4.51 | x | x |
| CS224 | SK020371 | 20/01/2015 | 5.32 | x | x |
| CS225 | NS061189 | 20/01/2015 | 6.69 | x | x |
| *CS244* | *KD241283* | *18/03/2015* | *9.3\** | *x* | *x* |
| CS307 | DS220595 | 14/04/2015 | — | x | — |
| *CS308* | *KD241283* | *28/04/2015* | — | *x* | *x* |
| CS313 | KM191186 | 19/05/2015 | 8.3* | x | — |

*In house WBC count

Targeted amplicon libraries were prepared from a 3 mm punch of each DBS sample. A 3 mm DBS punch contains about 200 ng of DNA. As a comparison, targeted amplicon libraries were also prepared from 100 ng of each genomic DNA sample (i.e., samples CS219, CS220, CS221, CS222, CS223, CS224, and CS225.

Figure 2:
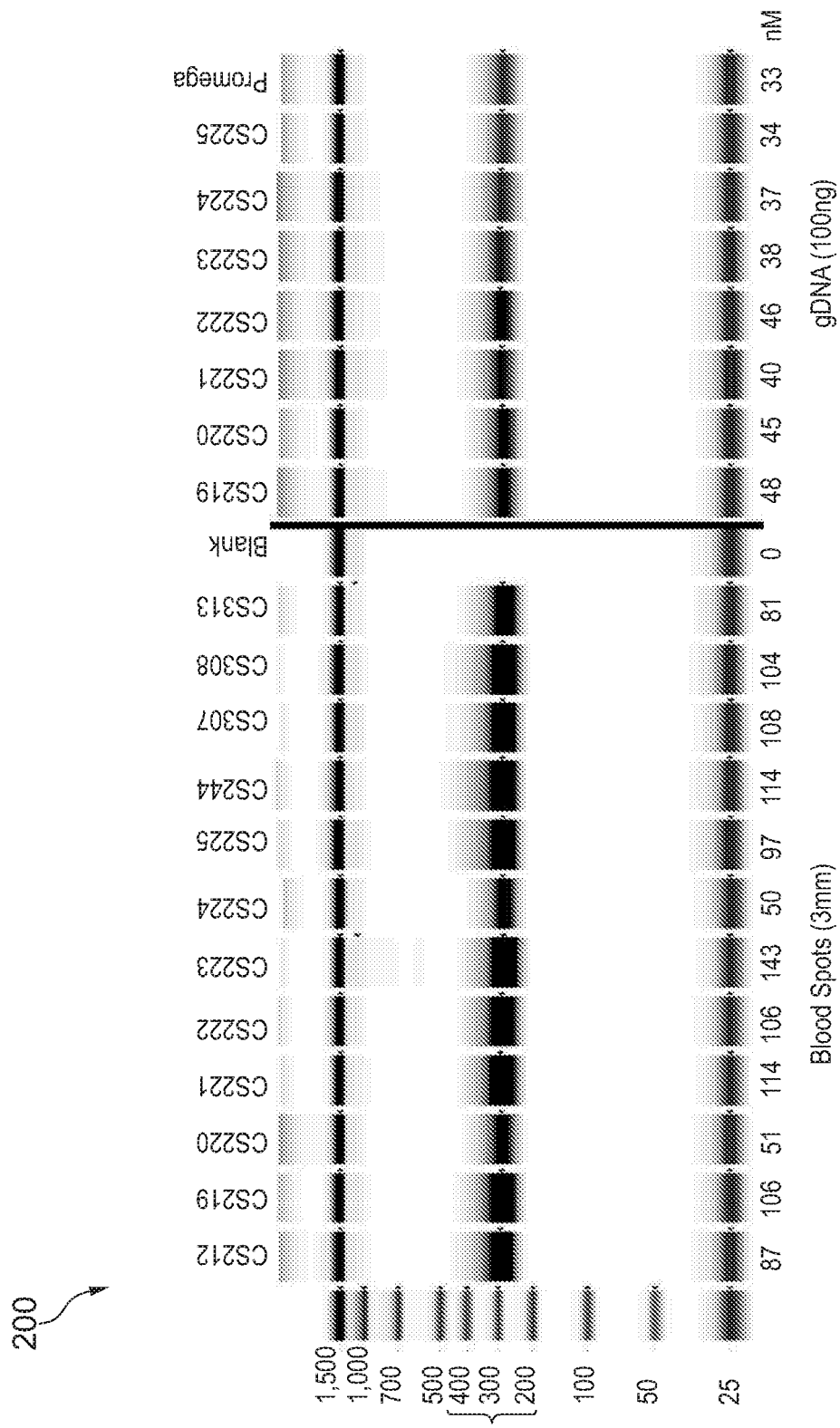
FIG. 2 shows an Agilent TapeStation image of a gel of the PCR amplification products generated from each DBS punch and genomic DNA samples using the method of FIG. 1.

FIG. 2 shows a Agilent TapeStation image 200 of a gel of the PCR amplification products generated from each DBS punch and genomic DNA samples using method 100 of FIG. 1. The DBS samples and genomic DNA (gDNA, 100 ng) control samples are as described with reference to Table 2. A bracket indicates the position of the bands representing the PCR amplification products. The lane labeled "Promega" is a positive control using a control DNA from Promega. The lane labeled "Blank" is a negative control using a filter punch that does not include DNA. The data show amplification products were obtained directly from DBS samples. Amplification products were also obtained from genomic DNA.

Figure 3:
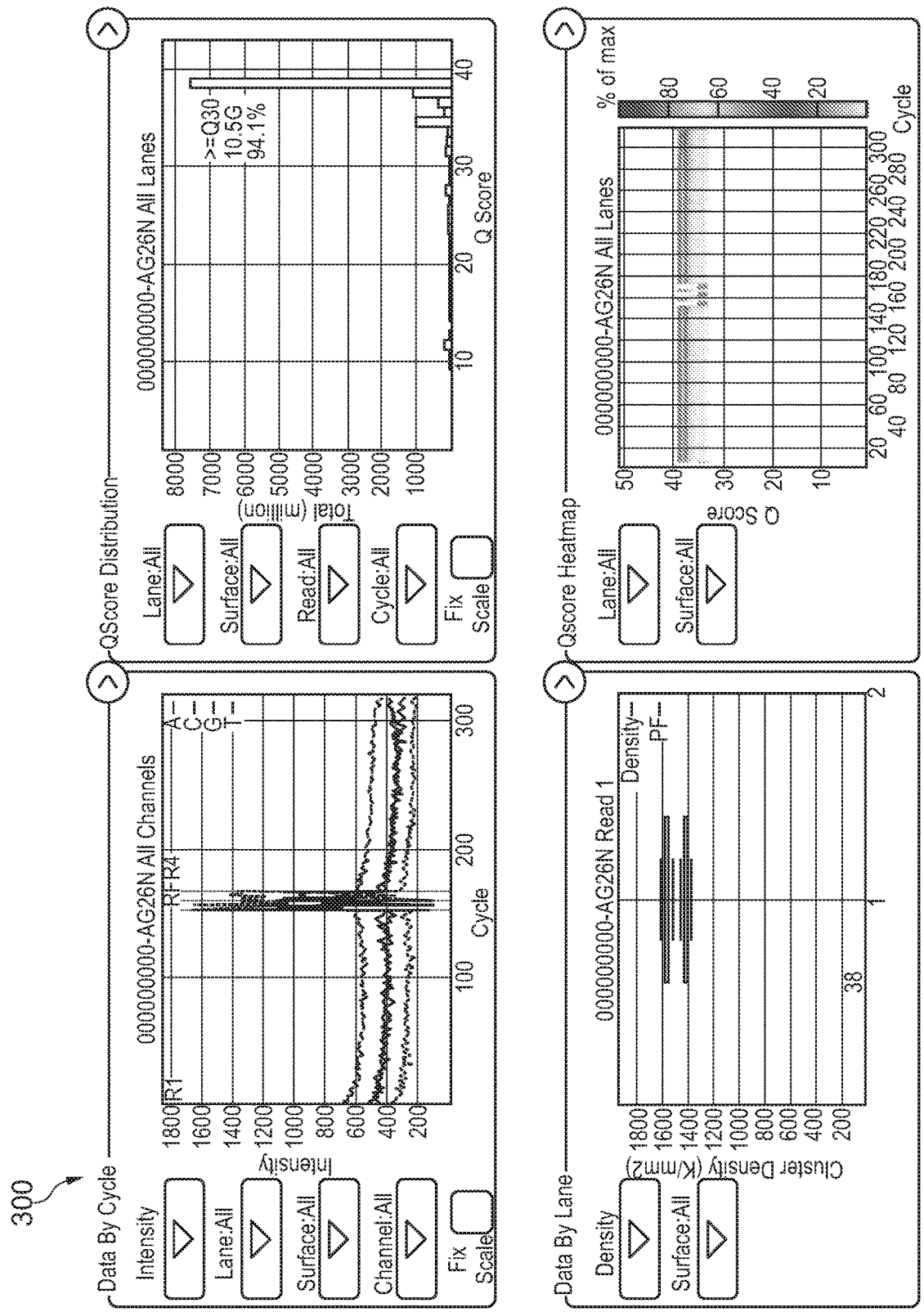
FIG. 3 shows a screenshot of an example of the MiSeq status pane with quality metrics for the sequence run using the pooled DBS library samples of FIG. 2.

FIG. 3 shows a screenshot 300 of illumina sequence analysis viewer (SAV) software summarizing quality metrics for the MiSeq sequence run using the pooled DBS library samples of FIG. 2. In this sequencing run, 35 million reads passed filter (about 1.5 million reads per sample). This yielded at least about 5,000× coverage for each identity SNP in the oligonucleotide panel.

Figure 4:
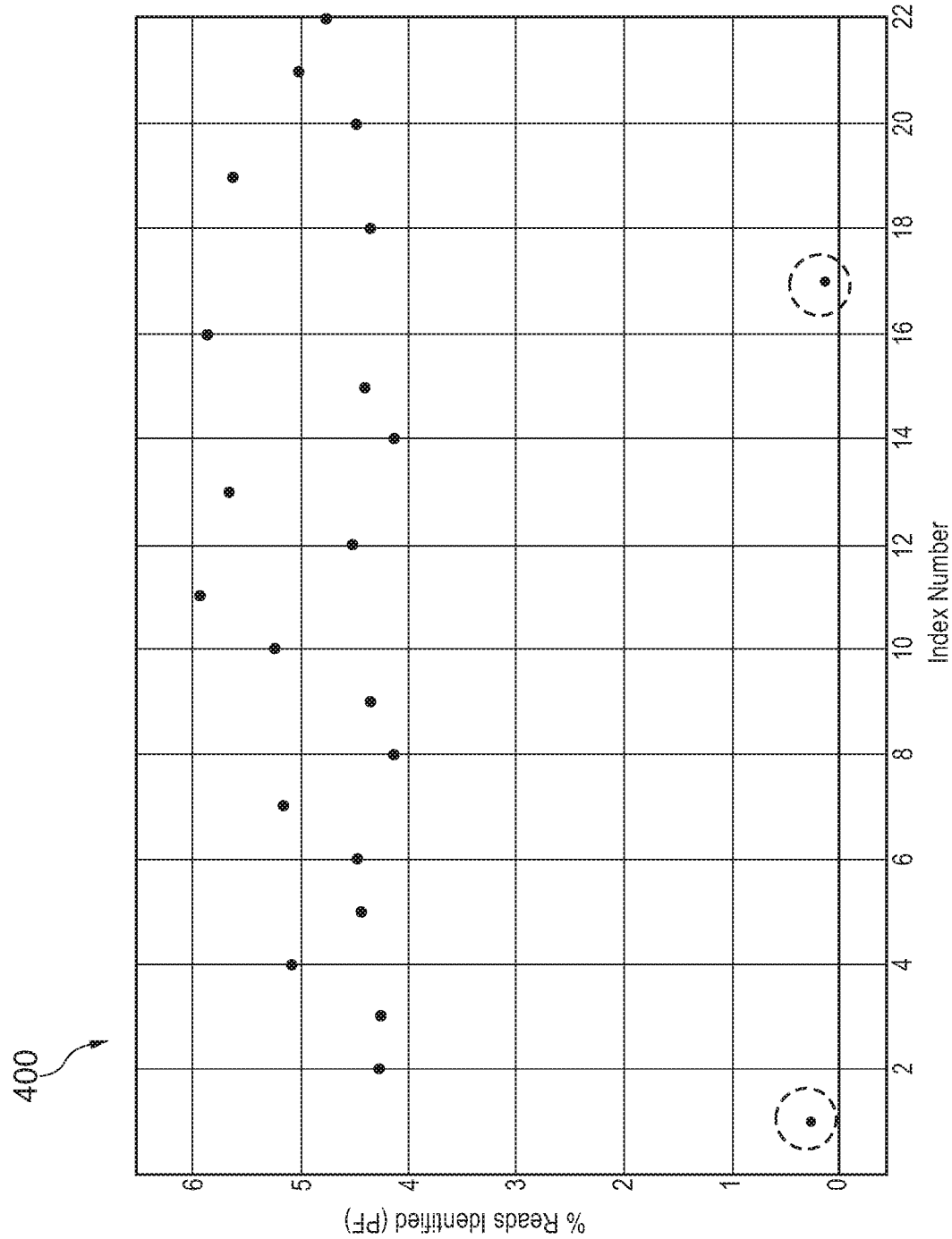
FIG. 4 shows a plot of the percent reads (passing filter) identified as a function of index number for the sequencing run of FIG. 3.

FIG. 4 shows a plot 400 of the percent reads (passing filter) identified as a function of index number for the sequencing run of FIG. 3. The data show even representation of each sample in the pooled sequencing library. The circled points on plot 400 are the negative controls.

The sequencing data was analyzed on MiSeq Reporter using Smith-Waterman aligner and the GATK variant caller. Variant calls at the 24 SNPs were scored relative to the hg19 reference. The calls were homozygous reference allele ("ref"), heterozygous ("het"), or homozygous alternative allele ("alt"). Calls from DBS samples, genomic DNA (extracted from the blood sample), and whole genome sequence (WGS) data (where available) were compared. FIG. 5 shows a table 500 of the SNP calls for 7 donor samples (i.e., CS219, CS220, CS221, CS222, CS223, CS224, and CS225) for both genomic DNA (gDNA) and DBS sample ("spot"). The data show that identical genotype calls were made from libraries prepared from genomic DNA extracted from a blood sample and libraries prepared from the corresponding DNA on the dried blood spot sample.

For each donor sample (i.e., genomic DNA and DBS samples) shown table 500 of FIG. 5, the data for all 24 identity SNP positions was collapsed into a single metric and used to determine identity. For example, for any given pair of donor samples, identity by state (IBS) can be observed at a given SNP and the relatedness of the samples determined. A DNA segment (e.g., SNP allele) is identical by state in two or more individuals (donors) if they have identical nucleotide sequences in this segment.

Figure 6A:
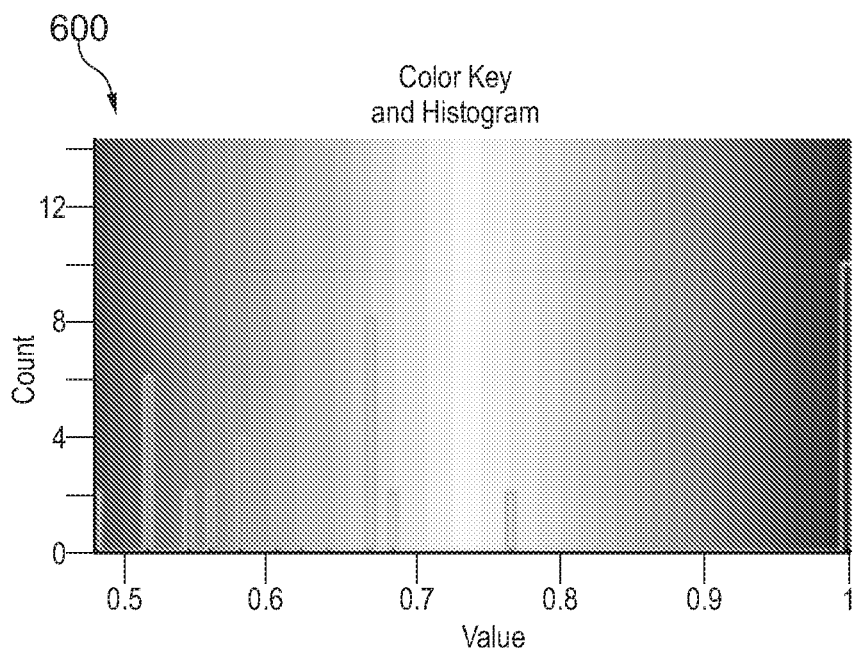
FIGS. 6A and 6B show a color key and histogram and a plot of identity by state (IBS) calculations, respectively, for the donor samples shown in the table of FIG. 5.
Figure 6B:
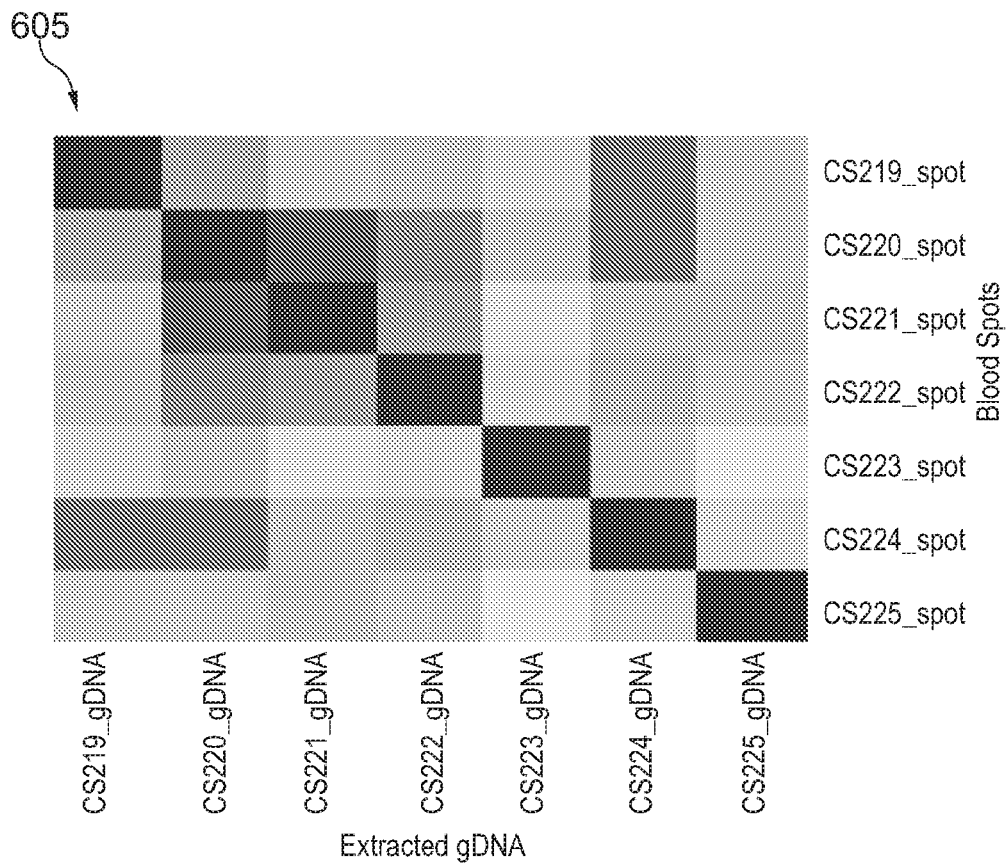

FIGS. 6A and 6B show a color key and histogram 600 and a plot 605 of identity by state (IBS) calculations, respectively, for the donor samples shown in table 500 of FIG. 5. Referring to FIG. 6A, the red color indicates 100% identity (value=1), which means that all 24 SNPs for any given pair of donor samples are the same. The color scale transitions to green which indicates 50% (value=0.5) of the SNPs for any given pair of donor samples are the same. Referring to FIG. 6B, plot 605 compares SNPs in genomic DNA ("Extracted gDNA") and DBS ("Blood Spots") samples based on identity by state. On the diagonal (red boxes), all 24 SNPs in the corresponding genomic DNA and DBS samples are the same, e.g., CS219_gDNA compared to CS219_spot and CS220_gDNA compared to CS220_spot, etc. In contrast, the 24 SNPs in unrelated samples, e.g., CS219_gDNA compared to CS220_spot, are not the same as indicated by the green box, which indicates that the samples are not the same.

Figure 7A:
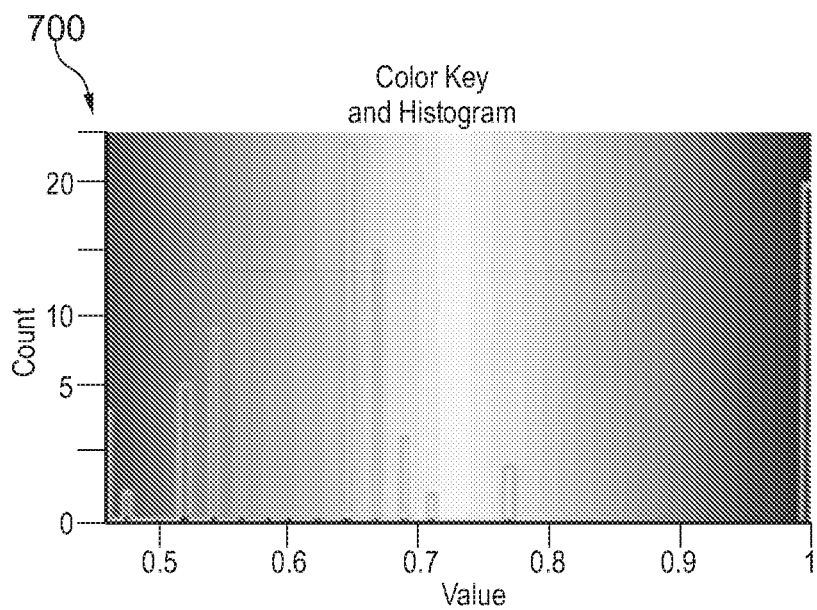
FIGS. 7A and 7B show a color key and histogram and a plot of identity by state (IBS) calculations, respectively, and show an example of discriminating DBS samples of Table 2 based on SNP data.
Figure 7B:
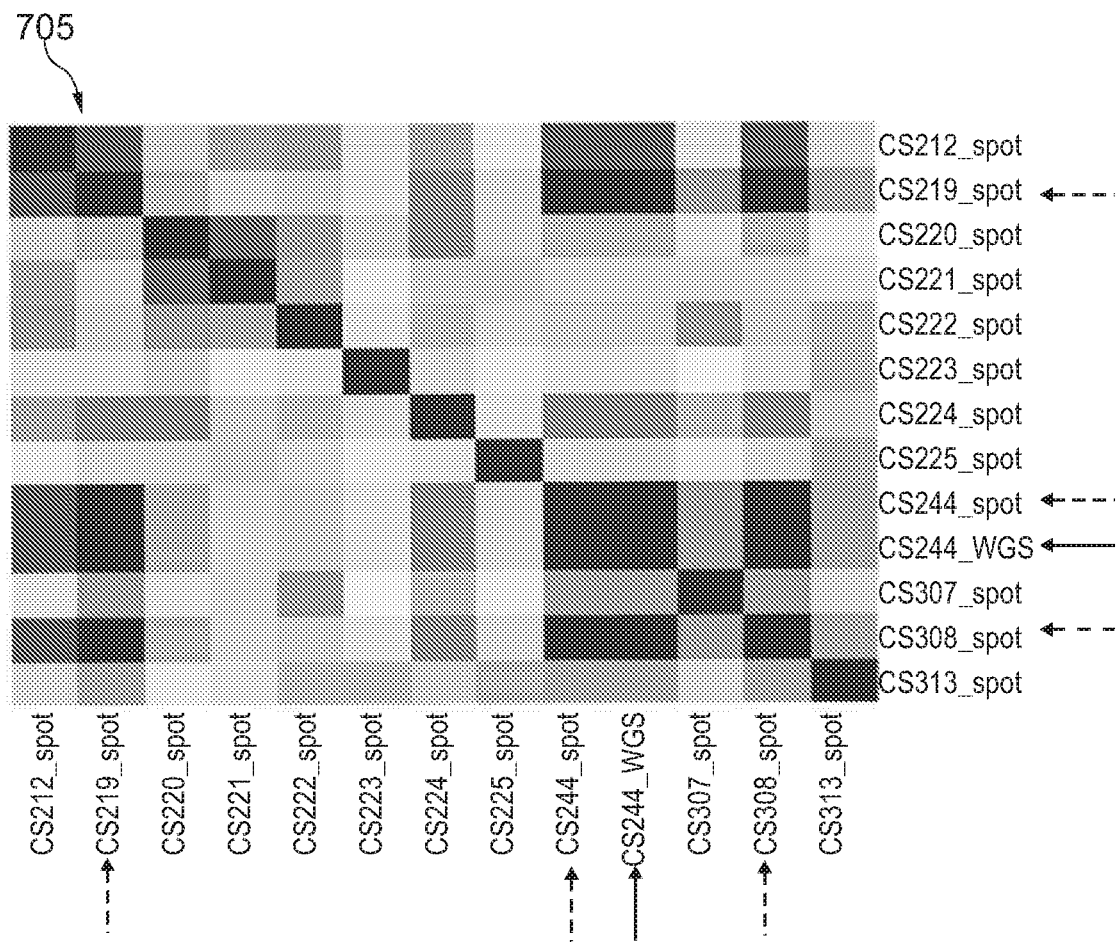

FIGS. 7A and 7B show a color key and histogram 700 and a plot 705 of identity by state (IBS) calculations, respectively, and show an example of discriminating DBS samples of Table 2 based on SNP data. Color key and histogram 700 is as described with reference to FIG. 6A. Referring now to FIG. 7B, plot 705 compares SNPs between DBS ("spot") samples based on identity by state. On the diagonal (red boxes), all 24 SNPs in the matching DBS samples are the same, e.g., CS212_spot compared to CS212_spote, CS219_spot compared to CS219_spot, etc. The dashed arrows at CS219_spot, CS244-spot, and CS308_spot indicate samples from the same donor that were taken at different time points. All SNPs in samples CS219_spot, CS244-spot, and CS308_spot are the same (red boxes), e.g., CS219_spot compared to CS308_spot, CS219_spot compared to CS244_spot, etc., and indicated that the samples are from the same individual. The solid arrow at CS244_WGS indicates whole genome sequencing data; this sample was used to check concordance with the whole genome vs TSCA amplicon data.

The data show that method 100 of FIG. 1 may be used to distinguish samples from different individuals and to correctly identify samples from the same individual taken at different time points.

In another example, targeted DNA amplicons may be prepared directly from FFPE samples using a TSCA library preparation protocol. To demonstrate preparation of targeted DNA amplicons directly for FFPE samples, slices (e.g., a 10 μm slice) from a breast tumor FFPE sample and a gastric tumor FFPE sample were used. In this example, the targeted DNA panel was a colorectal cancer panel (Illumina). Slices of each breast tumor and gastric tumor samples were placed directly in wells of a 96-well plate and an aliquot of hybridization buffer and an aliquot of an upstream and downstream oligonucleotide pool specific to targeted genes is added (e.g., total reaction volume of 50 μL) to each well. After the hybridization period and ligation/extension reaction, the targeted DNA was amplified using 30 cycles of PCR. Genomic DNA was also prepared from breast and gastric FFPE samples and used as controls in the TSCA amplification protocol (i.e., input genomic DNA=100 ng).

Figure 8:
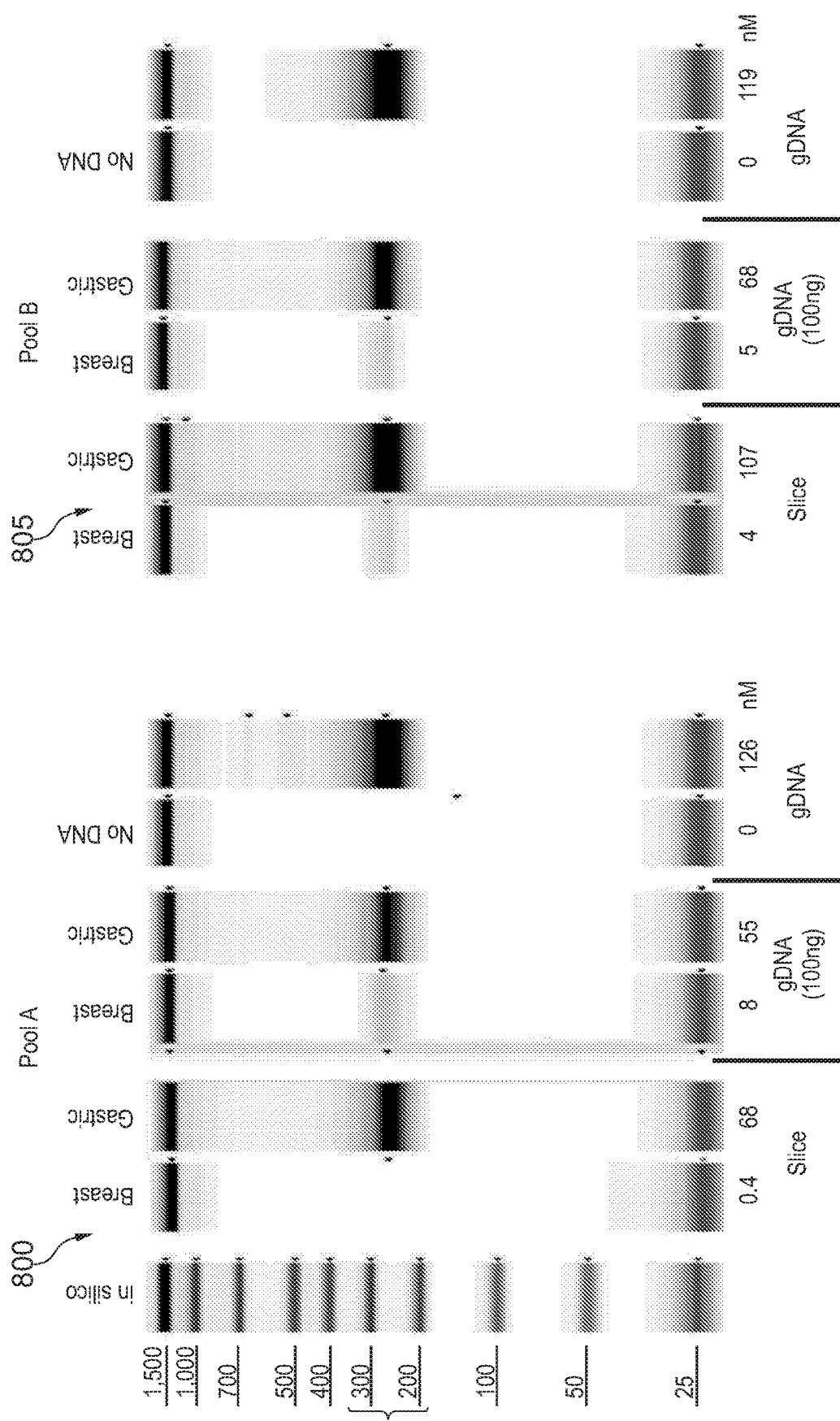
FIG. 8 shows an Agilent TapeStation image of a gel of the PCR amplification products from FFPE and genomic DNA samples in pool A and a BioAnalyzer image of the PCR amplification products from FFPE and genomic DNA samples in pool B.

FIG. 8 shows an Agilent TapeStation image 800 of a gel of the PCR amplification products from FFPE and genomic DNA samples in pool A and an Agilent TapeStation image 805 of the PCR amplification products from FFPE and genomic DNA samples in pool B, wherein pool A and B are separate oligo pools that target opposite strands of the respective DNA target, which provide two sets of equivalent data useful for excluding errors induced through PCR, sequencing or FFPE induced base modifications. A bracket in FIG. 8 indicates the position of the bands representing the PCR amplification products. The lane labeled "No DNA" is a negative control. The data show amplification products were obtained directly from FFPE samples. Amplification products were also obtained from genomic DNA.

Multiplex Targeted PCR Amplification Libraries and Sequencing for Sample Validation In another embodiment, the methods of the invention use multiplex targeted PCR amplification for preparation of genomic amplicon libraries for subsequent sequencing and sample validation.

Figure 9:
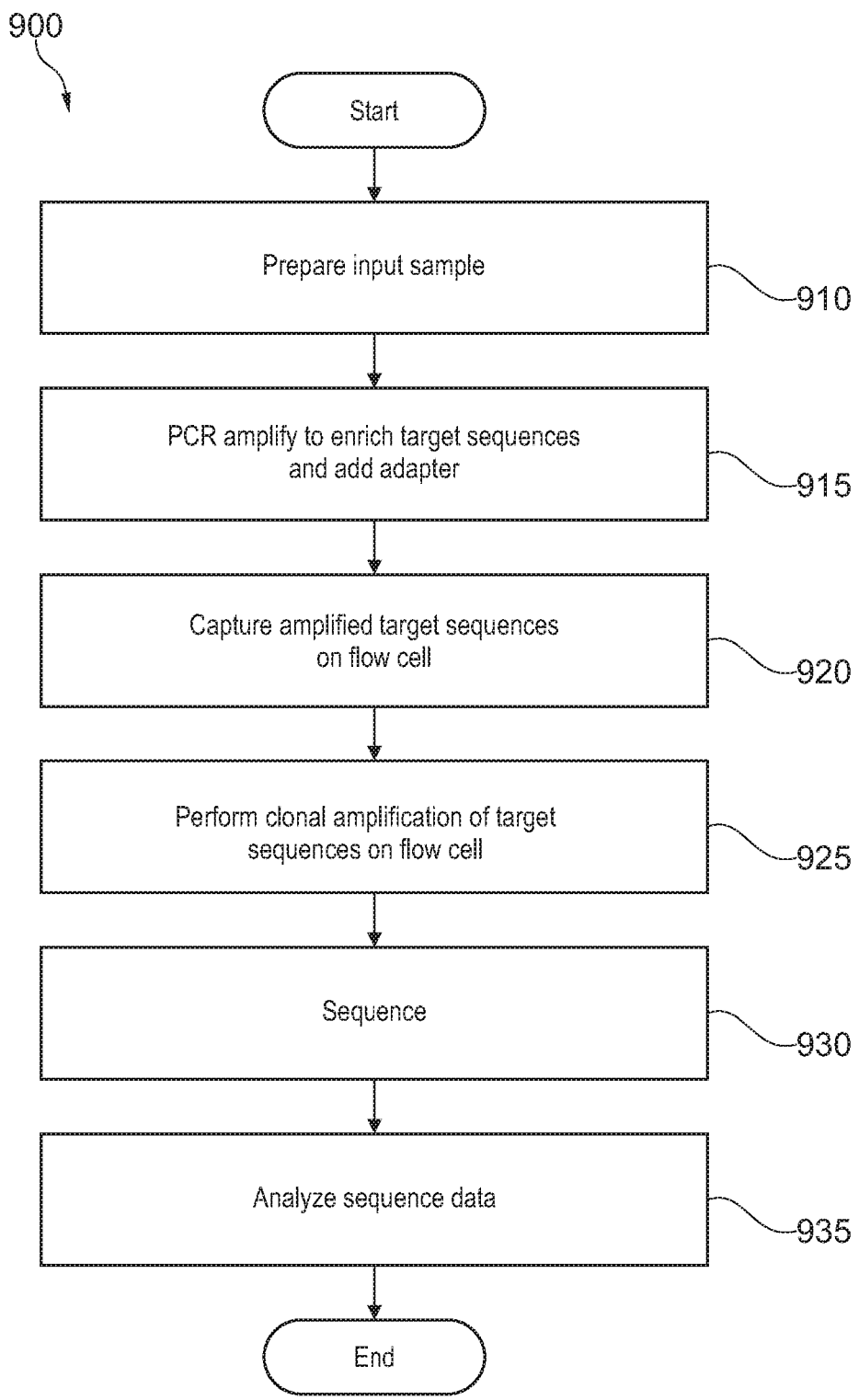
FIG. 9 illustrates a flow diagram of an example of method of using multiplex targeted PCR amplification for preparation of targeted amplicon libraries and subsequent sequencing for sample identification.

FIG. 9 illustrates a flow diagram of an example of method 900 of using multiplex targeted PCR amplification for preparation of targeted amplicon libraries and subsequent sequencing for sample identification. Method 900 includes, but is not limited to, the following steps.

At a step 910, an input sample is prepared. In one example, the input sample is a 3 mm punch from a DBS sample. The DBS punch is placed directly in the well of a 96-well plate.

At a step 915, multiplex targeted PCR amplification is performed on the DBS sample. For example, a targeted primer mix, PCR reagents, and Phusion Hot Start II High-Fidelity DNA Polymerase (Life Technologies) are added to each well with a DBS punch therein. The targeted primer mix includes primer pairs for 45 identity SNPs that include index adapters (i.e., 45-plex ID SNP subset from ForenSeq set (Illumina, Inc)).

At a step 920, the amplified DNA is pooled and loaded onto a flow cell prepared with capture probes. The capture probes are specific for the amplified target sequences. The targeted DNA sequences are captured on the flow cell by hybridization to the capture probes on the flow cell surface.

At a step 925, captured target sequences are clonally amplified on the flow cell surface.

At a step 930, the amplified DNA is sequenced. For example, the amplified DNA is sequenced on a MiSeq V3 instrument using 2×76 cycles of sequencing.

At a step 935, the sequencing data is analyzed. For example, the sequencing data is analyzed using the Burrow-Wheeler Aligner (BWA) in the PCR amplicon work flow in MiSeq Reporter.

Method 900 was evaluated using the blood samples described above with reference to Table 2. Targeted amplicon libraries were prepared from a 3 mm punch of each DBS sample. A 3 mm DBS punch contains about 200 ng of DNA. Targeted amplicon libraries were also prepared from 1 ng of genomic DNA from samples CS219, CS220, CS221, CS222, CS223, CS224, and CS225.

Figure 10A:
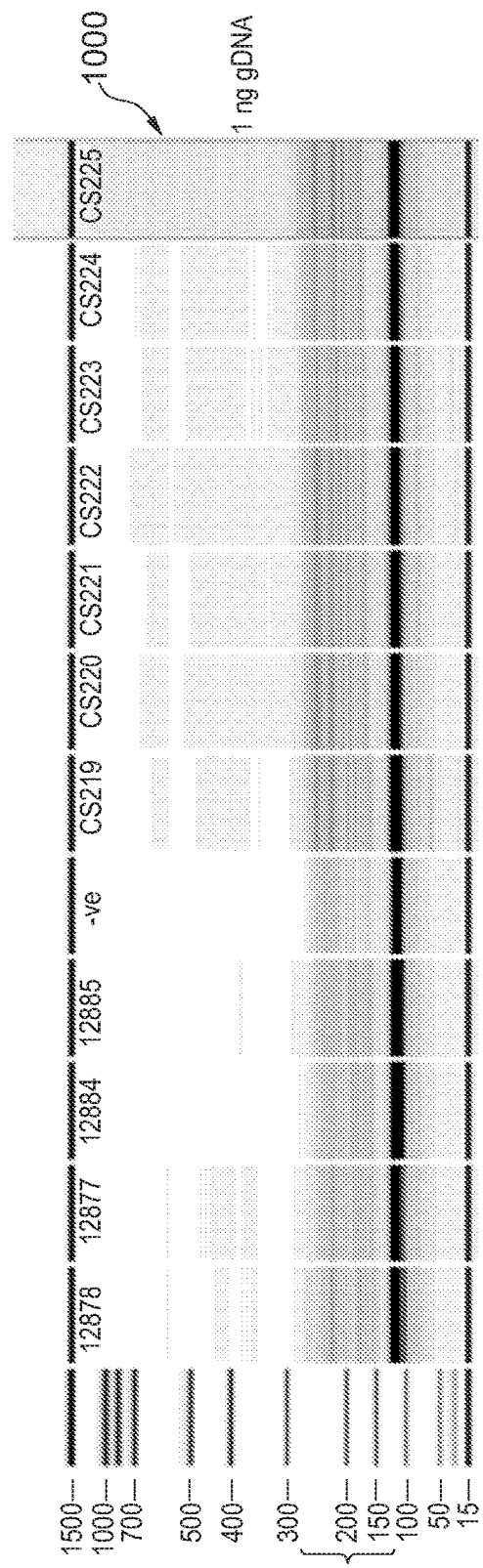
FIGS. 10A and 10B show a BioAnalyzer image of a gel of the PCR amplification products generated from gDNA and a BioAnalyzer image of the PCR amplification products generated from each DBS punch, respectively, using the method of FIG. 9.
Figure 10B:
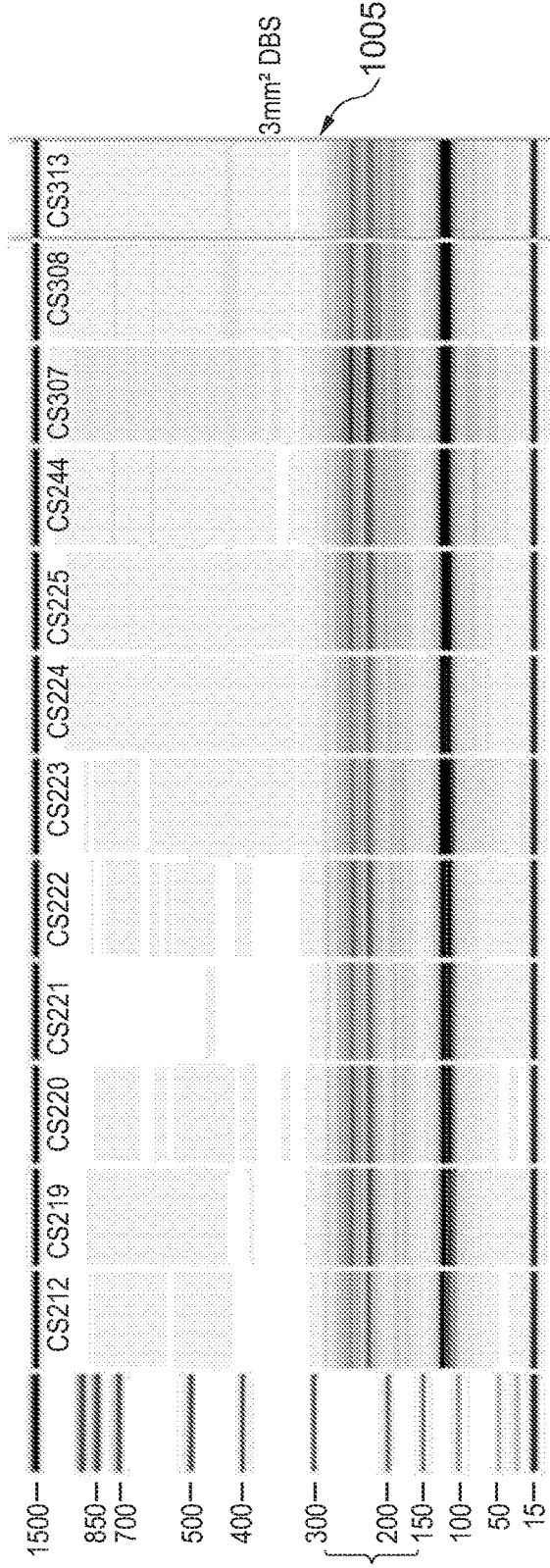

FIGS. 10A and 10B show a BioAnalyzer image 1000 of a gel of the PCR amplification products generated from gDNA and a BioAnalyzer image 1005 of the PCR amplification products generated from each DBS punch, respectively, using method 900 of FIG. 9. The DBS samples and genomic DNA (gDNA, 1 ng) control samples are as described above with reference to Table 2. A bracket indicates the position of the bands representing the PCR amplification products. Referring to FIG. 10A, the lane labeled "-ve" is a negative control that does not include template DNA. Lanes 12878, 12877, 12884, and 12885 are control samples from the Platinum Genomes family (i.e., father, mother, and 2 children). Some amplification products were observed in the negative control sample. The data show amplification products were obtained directly from DBS samples. Amplification products were also obtained from genomic DNA.

Figure 11:
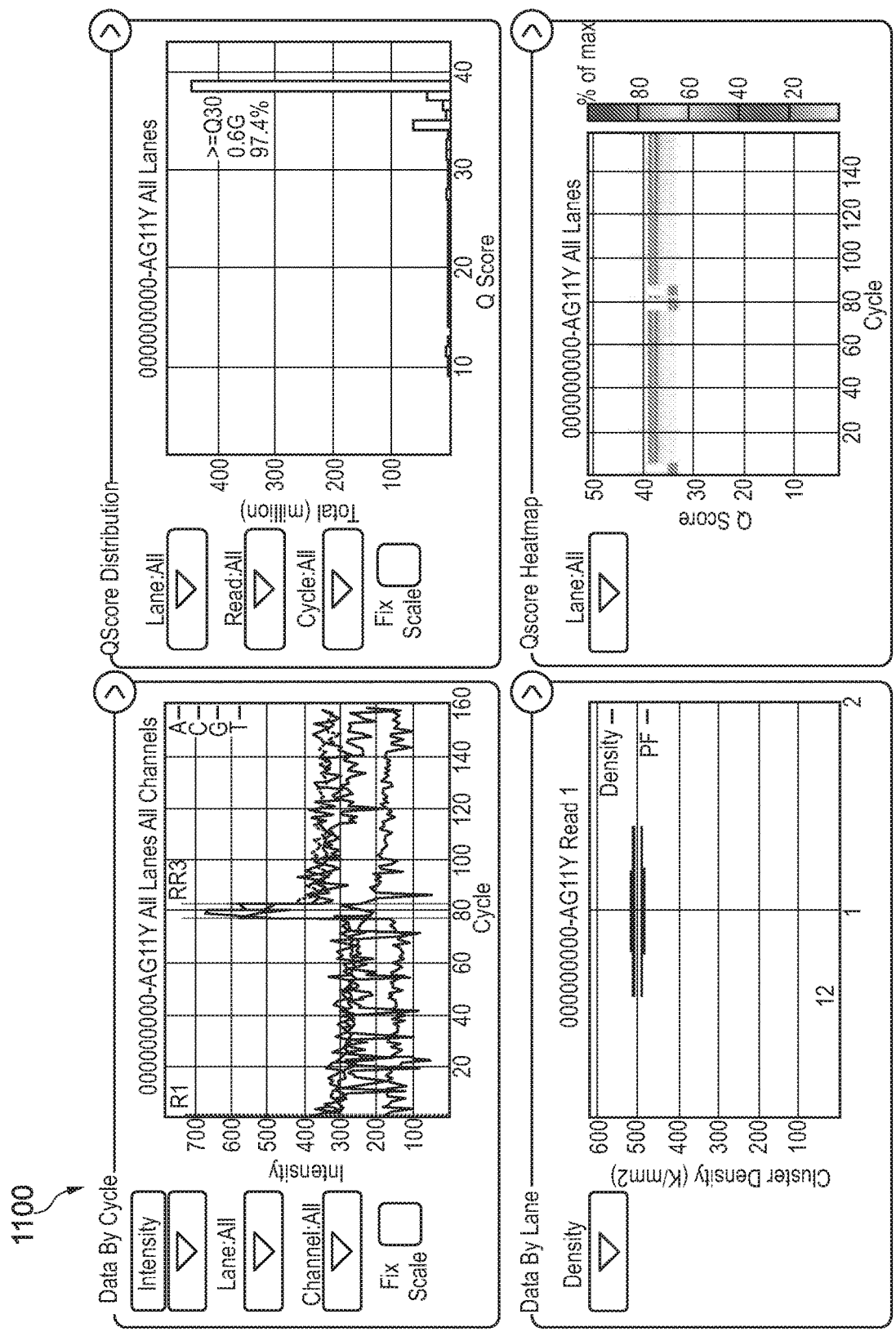
FIG. 11 shows a screenshot of illumina sequence analysis viewer (SAV) software summarizing quality metrics for the MiSeq sequence run using the DBS and genomic amplicon libraries of FIGS. 10A and 10B.

FIG. 11 shows a screenshot 1100 of illumina sequence analysis viewer (SAV) software summarizing quality metrics for the MiSeq sequence run using the DBS and genomic amplicon libraries of FIGS. 10A and 10B. In this sequencing run, one surface of the flow cell was scanned, 3.71 million reads passed filter for about 10 s-1000 s×coverage (a low coverage run) for each identity SNP in the oligonucleotide panel.

Figure 12:
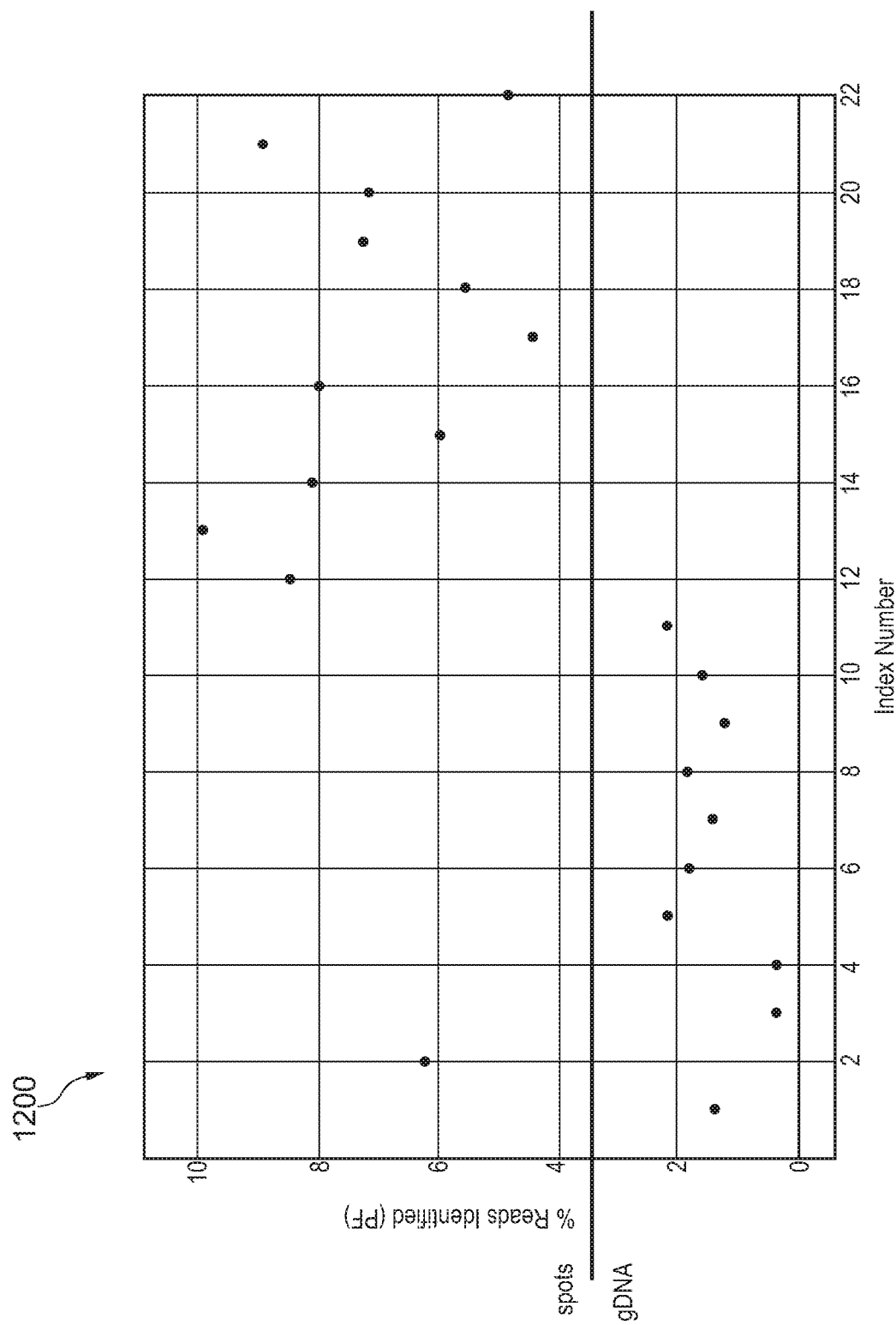
FIG. 12 shows a plot of the percent reads (passing filter) identified as a function of index number for the sequencing run of FIG. 11.

FIG. 12 shows a plot 1200 of the percent reads (passing filter) identified as a function of index number for the sequencing run of FIG. 11. Reads from the DBS samples ("spots") are above the line and reads from the genomic DNA samples ("gDNA") are below the line. The discrepancy in read representation for DBS and genomic DNA samples may be due to a lower efficiency in sample pooling and/or normalization.

The sequencing data was analyzed on MiSeq Reporter using the Burrow-Wheeler Aligner (BWA) in the PCR amplicon workflow in MiSeq Reporter.

For each donor sample (i.e., genomic DNA and DBS samples), the data for all 45 identity SNP positions was collapsed into a single metric and used to determine identity.

Figure 13A:
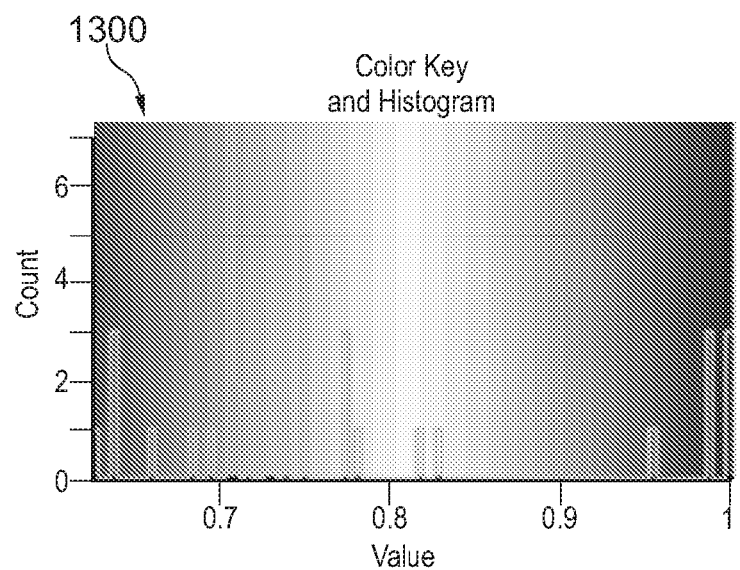
FIGS. 13A and 13B show a color key and histogram and a plot of identity by state (IBS) calculations, respectively, for the donor samples of Table 2 used to evaluate method 900 of FIG. 9.
Figure 13B:
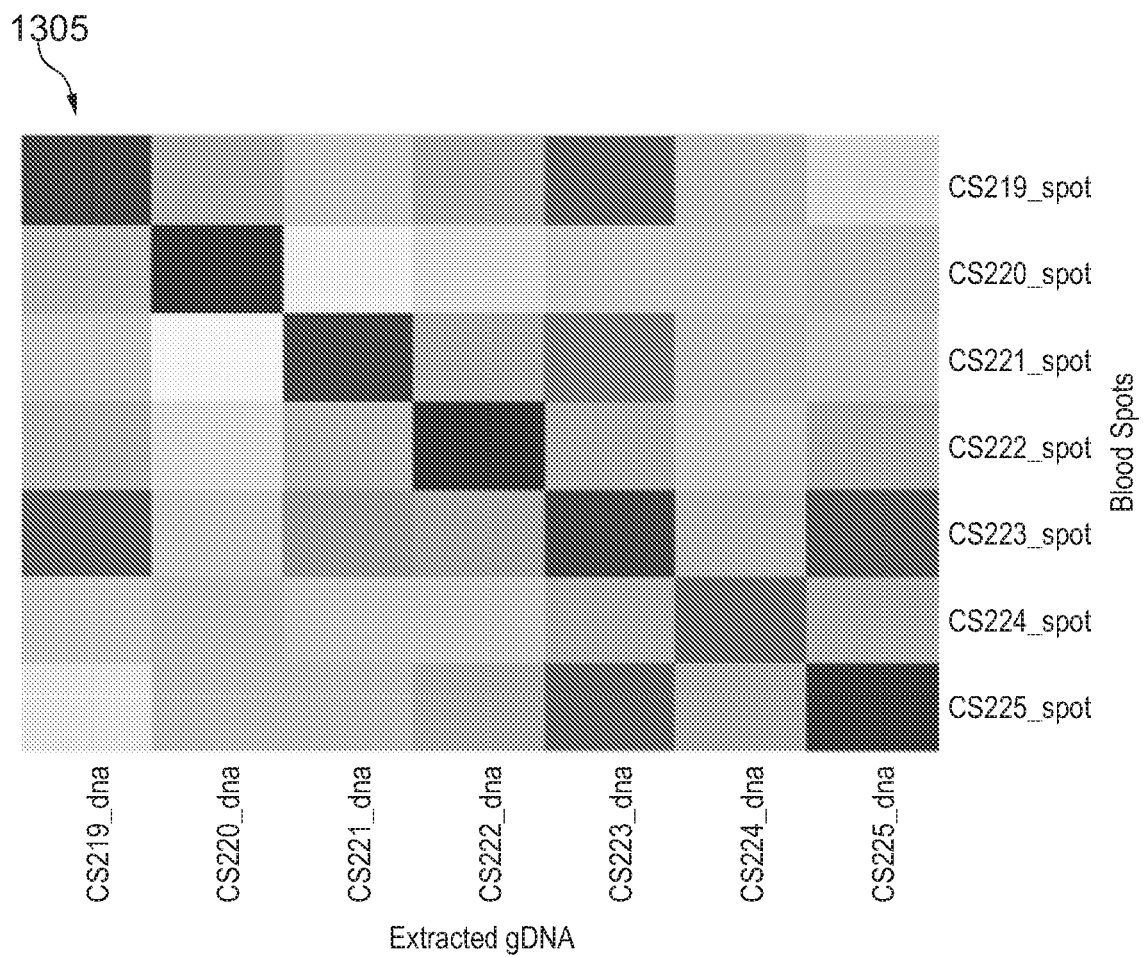

FIGS. 13A and 13B show a color key and histogram 1300 and a plot 1305 of identity by state (IBS) calculations, respectively, for the donor samples of Table 2 used to evaluate method 900 of FIG. 9. Referring to FIG. 13A, the red color indicates 100% identity (value=1), which means that all 45 SNPs for any given pair of donor samples are the same. The color scale transitions to green which indicates 50% (value=0.5) of the SNPs for any given pair of donor samples are the same. Referring to FIG. 13B, plot 1305 compares SNPs in genomic DNA ("Extracted gDNA") and DBS ("Blood Spots") samples based on identity by state. On the diagonal (red boxes), all 45 SNPs in the corresponding genomic DNA and DBS samples are the same, e.g., CS219_dna compared to CS219_spot and CS220_dna compared to CS220_spot, etc., which indicates that the sample identity is called correctly. In contrast, the 45 SNPs in unrelated samples, e.g., CS219_dna compared to CS220_spot, are not the same as indicated by the green box, which indicates that the samples are not the same. Note that for CS224_dna compared to CS224_spot, the box is not as red as the other matched genomic DNA/DBS samples which may be due to lower sequencing coverage of some amplicons.

Figure 14A:
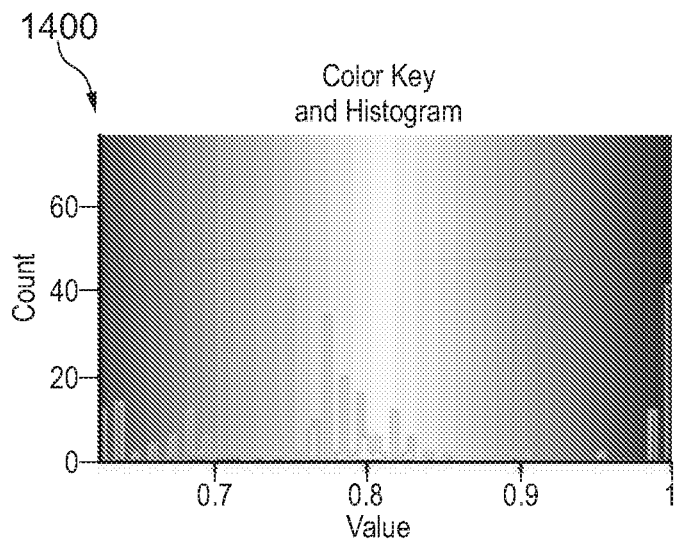
FIGS. 14A and 14B show a color key and histogram and a plot of identity by state (IBS) calculations, respectively, and show an example of discriminating DBS samples of Table 2 based on SNP data.
Figure 14B:
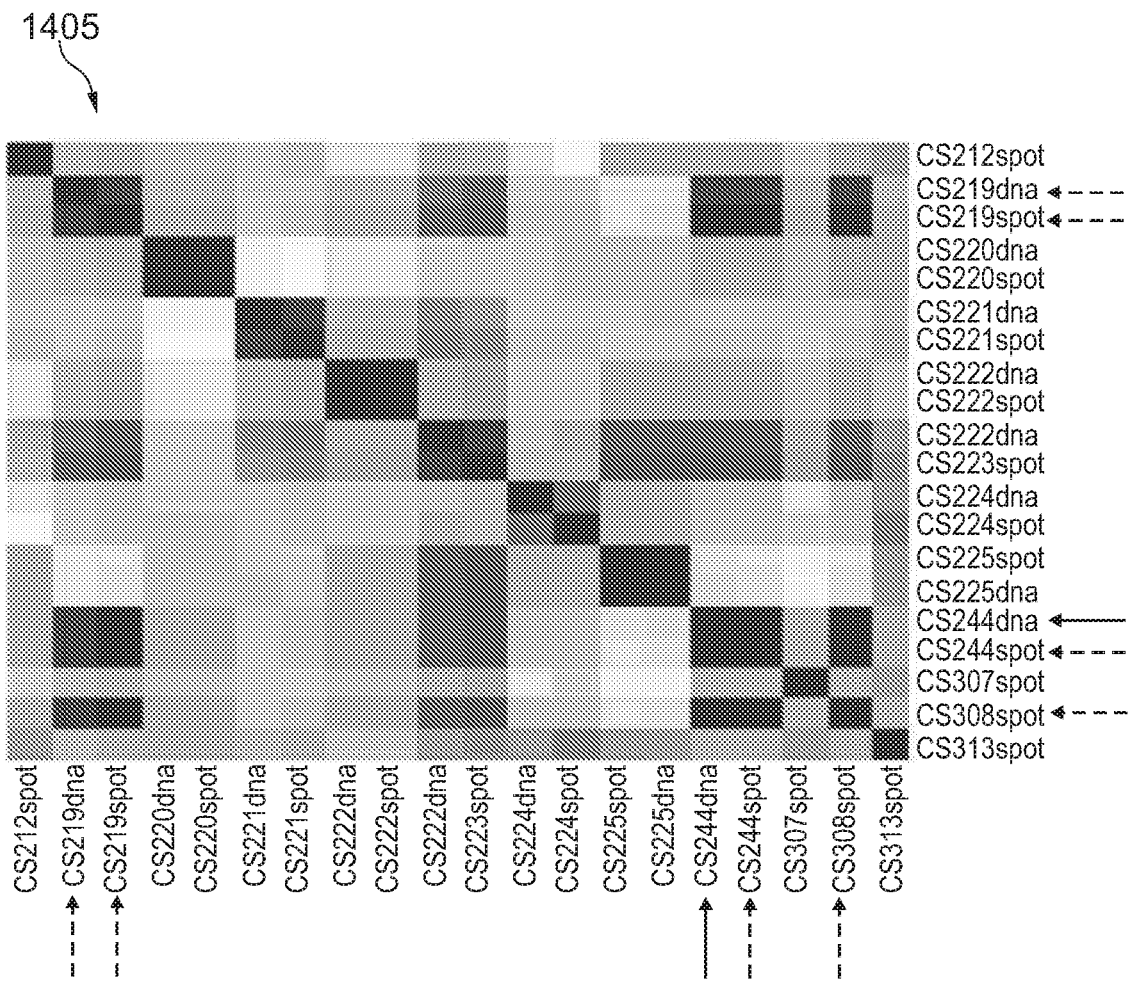

FIGS. 14A and 14B show a color key and histogram 1400 and a plot 1405 of identity by state (IBS) calculations, respectively, and show an example of discriminating DBS samples of Table 2 based on SNP data. Color key and histogram 1400 is as described with reference to FIG. 13A. Referring now to FIG. 14B, plot 1405 compares SNPs between DBS ("spot") and genomic DNA ("dna") samples based on identity by state. On the diagonal (red boxes), all 45 SNPs in the matching DBS samples are the same, e.g., CS212spot compared to CS212spot, CS219dna compared to CS219dna, etc. The dashed arrows at CS219dna, CS219spot, CS244spot, and CS308spot indicate samples from the same donor (reference sample) that were taken at different time points. All 45 SNPs in the reference samples CS219, CS244, and CS308 are identified as the same (red boxes), e.g., CS219spot compared to CS308spot, CS219dna compared to CS244spot, etc., and indicated that the samples are from the same individual. The solid arrow at CS244dna indicates whole genome sequencing data; this sample was used to check concordance with the whole genome vs PCR amplicon data.

The data show that method 900 of FIG. 9 may be used to distinguish samples from different individuals and to correctly identify samples from the same individual taken at different time points.

High Resolution Sample Discrimination

In another embodiment, the methods of the invention are used to discriminate between samples from closely related individuals. In one example, the closely related individuals are siblings. In another example, the closely related individuals are a family trio, wherein both parents and at least one child are afflicted, for example, with a disease or condition.

To evaluate the efficacy of the methods of the invention in high resolution sample discrimination, a set of samples from the Platinum Genomes family was used. The Platinum Genomes is a high confidence, "platinum" quality reference variant call set that was generated by sequencing a large family to high depth using a PCR-Free sample prep to maximize variant calling sensitivity as described by Eberle et al. (2016) bioRxiv doi: 10.1101/055541, the content of which is incorporated herein by reference in its entirety. Sample discrimination was performed using method 100 of FIG. 1 and the 24 identity SNP panel.

Figure 15:
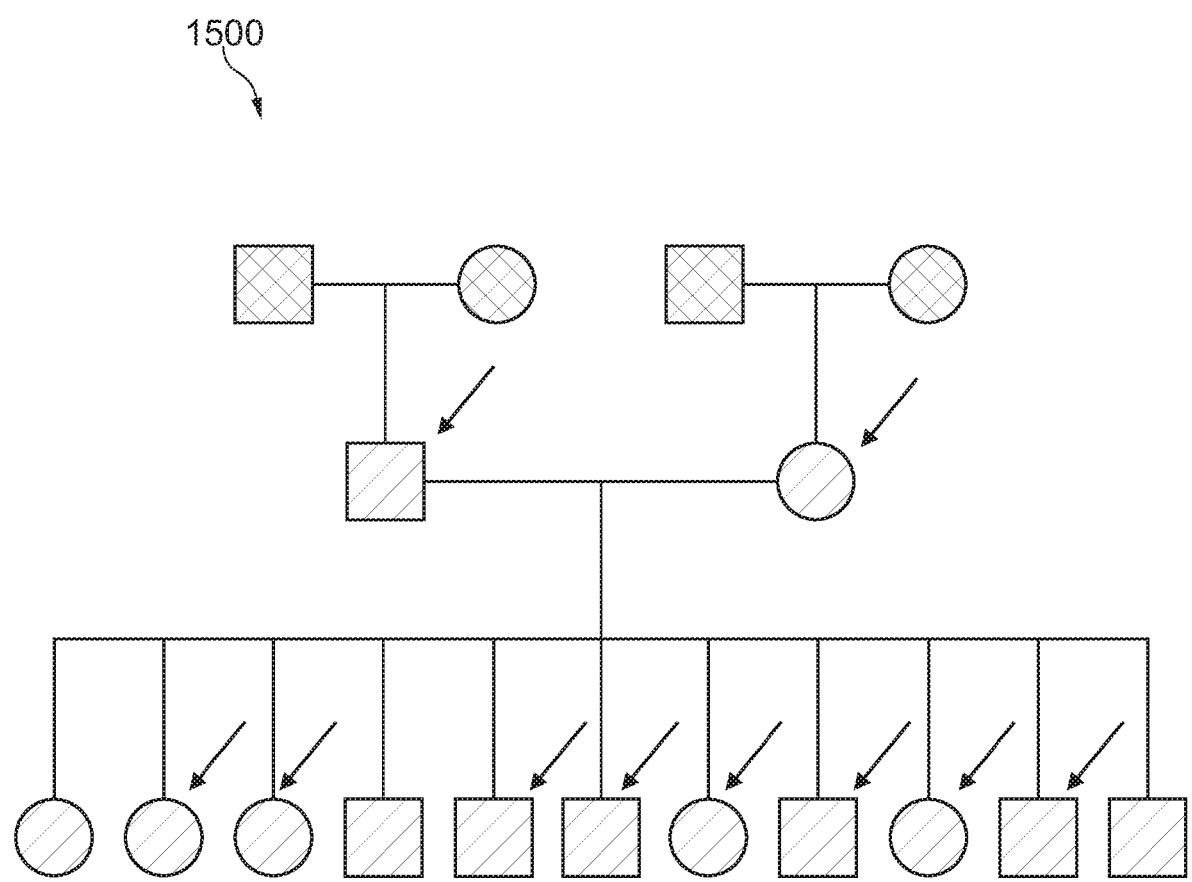
FIG. 15 shows a family tree diagram of the Platinum Genomes family.

FIG. 15 shows a family tree diagram 1500 of the Platinum Genomes family. The arrows indicate family members whose genomic DNA was used in the evaluation (i.e., father, mother, 4 female children, and 5 male children).

Figure 16A:
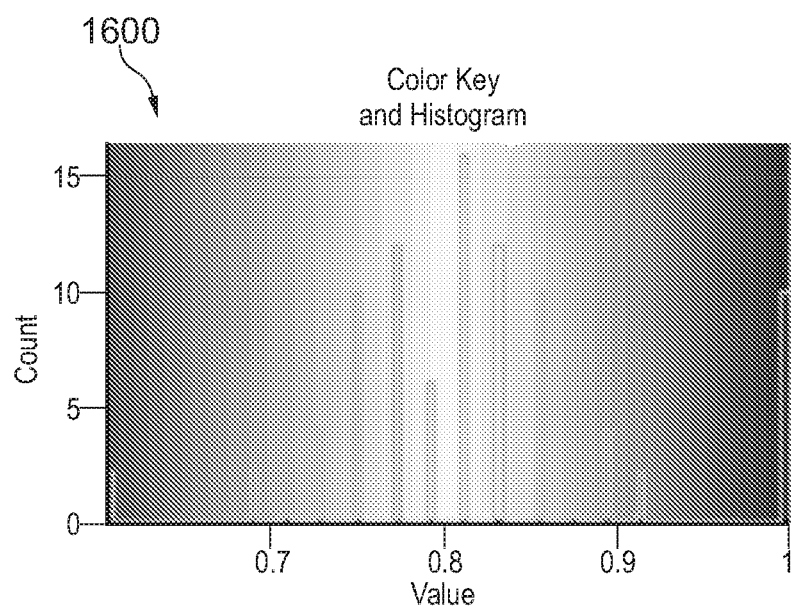
FIGS. 16A and 16B show a color key and histogram and a plot of identity by state (IBS) calculations, respectively, and show an example of high resolution genomic DNA sample discrimination based on SNP data.
Figure 16B:
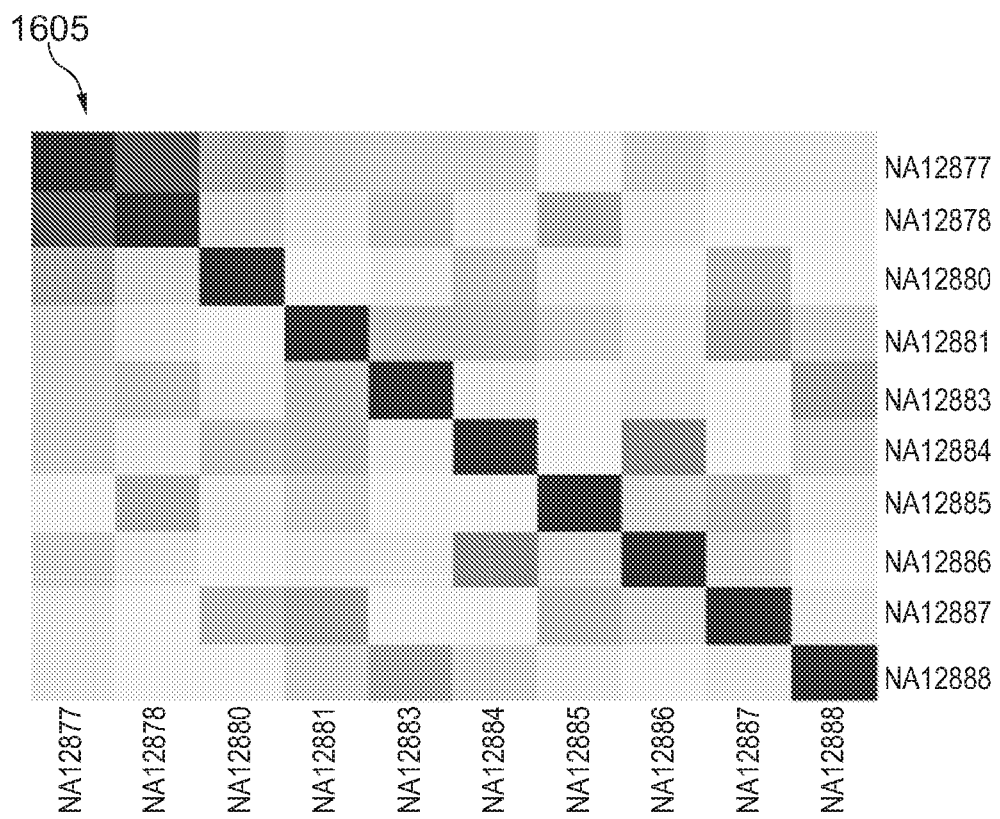

FIGS. 16A and 16B show a color key and histogram 1600 and a plot 1605 of identity by state (IBS) calculations, respectively, and show an example of high resolution genomic DNA sample discrimination based on SNP data. The genomic DNA samples are as described with reference to FIG. 15. Referring to FIG. 16A, the red color indicates 100% identity (value=1), which means that all 24 SNPs for any given pair of donor samples are the same. The color scale transitions to green which indicates 50% (value=0.5) of the SNPs for any given pair of donor samples are the same. Referring now to FIG. 16B, plot 1605 compares SNPs between genomic samples based on identity by state. On the diagonal (red boxes), all 24 SNPs in the matching genomic samples are the same, e.g., NA12877 compared to NA12877, NA12878 compared to NA12878, etc. The data show that method 100 of FIG. 1 may be used to distinguish samples from closely related individuals.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements. A number of embodiments are set forth in this description and in the incorporated materials of U.S. Provisional Patent Application No. 61/189,063 filed on Jul. 6, 2015. Nevertheless, it will be understood that various modifications may be made. Accordingly, other embodiments are within the scope of the following claims.

What is claimed is:

1. A method for validating an identity of a biological sample comprising:
   (a) providing an unprocessed biological sample comprising different target nucleic acids, wherein each of the different target nucleic acids comprises, from 3' to 5', contiguous first, second, and third target domains;
   (b) contacting in solution the unprocessed biological sample with a plurality of different probe sets comprising priming sequences and sequences substantially complementary to target domains to form solution-phase hybridization complexes with the different target nucleic acids, wherein at least one probe in each of the different probe sets comprises a distinct adapter sequence not native to the target nucleic acid, and wherein each probe set comprises:
      (i) a first probe comprising, from 5' to 3': a first priming sequence and a sequence that is substantially complementary to a first target domain; and
      (ii) a second probe comprising, from 5' to 3': a sequence substantially complementary to a third target domain, and a second priming sequence,
   wherein the plurality of different probe sets comprise a plurality of probes configured to selectively hybridize to polymorphic regions that are informative of the identity of the biological sample;
   (c) contacting the solution-phase hybridization complexes with an extension enzyme and nucleotides, wherein the first probe is extended along the second target domain of the hybridization complexes formed in (b);
   (d) ligating the extended first probe to the second probe to form amplification templates;
   (e) amplifying the amplification templates with first and second primers that are complementary to the first priming sequence and the second priming sequence to produce amplicons;
   wherein there is no purification and no amplification of the target nucleic acid from the unprocessed biological sample prior to the contacting step (b);
   (f) obtaining nucleic acid sequence information for a plurality of portions of the amplified sample, wherein the nucleic acid sequence information comprises the nucleic acid sequence of the second target domain; and
   (g) validating the identity of the biological sample based on the nucleic acid sequence information.

2. The method of claim 1, wherein the nucleic acid is DNA.

3. The method of claim 1, comprising, prior to step (c), a step of collecting a supernatant comprising solution-phase hybridization complexes from the unprocessed biological sample.

4. The method of claim 3, wherein the supernatant comprising solution-phase hybridization complexes is further contacted with a solid support to form immobilized hybridization complexes when contacted with the extension enzyme and the nucleotides of step (c).

5. The method of claim 4, wherein the solid support comprises beads or a filter plate.

6. The method of claim 1, wherein obtaining nucleic acid sequence information comprises massively parallel sequencing or detecting the amplicons on the surface of a nucleic acid array.

7. The method of claim 1, wherein the plurality of different probe sets comprises at least 100 different probe sets.

8. The method of claim 1, wherein the plurality of different probe sets comprises a plurality of probes configured to selectively hybridize to regions that comprise cancer-associated polymorphisms.

9. The method of claim 1, wherein the sample is a blood sample, a whole blood sample, or a saliva sample, and wherein the sample optionally comprises tumor tissue.

10. The method of claim 1, wherein the sample comprises dried blood or dried blood on a porous solid surface.

11. A method of tracking the identity of a biological sample during different stages of sample processing, comprising:
   (a) providing a nucleic acid-containing cellular sample;
   (b) separating a portion of the sample into a first portion and a second portion and obtaining a first set of nucleic acid sequence information from the first portion of the biological sample according to steps (a)-(g) of claim 1, wherein the first set of nucleic acid sequence information comprises identity informative sequence information;
   (c) purifying nucleic acid from the second portion and obtaining a second set of sequence information; and
   (d) using computer-assisted logic, comparing the identity informative sequence information from the first set of nucleic acid sequence information to the second set of sequence information to confirm that the first and second sets of sequence information were obtained from the same source.

12. The method of claim 11, wherein the identity informative sequence information comprises single nucleotide polymorphism (SNP) genotype information for at least 100 unique SNPs.

13. The method of claim 11, wherein the second set of sequence information comprises SNP genotype information for at least 100 unique SNPs, comprises a whole genome sequence, or comprises exome sequence information.

14. The method of claim 11, wherein the sample is a blood sample, a whole blood sample, or a saliva sample.

15. The method of claim 11, wherein the same source is the same individual.

16. The method of claim 1, wherein the polymorphic regions are single nucleotide polymorphisms.

17. The method of claim 1, wherein the sample comprises dried saliva or dried saliva on a porous surface.

18. The method of claim 11, wherein the sample comprises dried blood or dried blood on a porous solid surface, or dried saliva, or dried saliva on a porous solid surface.

19. The method of claim 1, wherein the extension enzyme of step (c) is a non-strand displacing polymerase.

20. The method of claim 1, wherein the nucleic acid sequence information obtained from the second target domain comprises two or more nucleotides in length.

\* \* \* \* \*